(12) United States Patent
Wendel et al.

(10) Patent No.: US 12,343,420 B2
(45) Date of Patent: Jul. 1, 2025

(54) STABILIZED POLYRIBONUCLEOTIDE CODING FOR AN ELASTIC FIBROUS PROTEIN

(71) Applicant: Eberhard Karls Universitaet Tuebingen Medizinische Fakultaet, Tuebingen (DE)

(72) Inventors: Hans-Peter Wendel, Balingen (DE); Timea Keller, Tuebingen (DE); Andrea Nolte, Deckenpfronn (DE); Meltem Avci-Adali, Kirchentellinsfurt (DE); Tobias Walker, Tuebingen (DE)

(73) Assignee: Eberhard Karls Universitaet Tuebingen Medizinische Fakultaet, Tuebingen (DE)

(*) Notice: Subject to any disclaimer, the term of this patent is extended or adjusted under 35 U.S.C. 154(b) by 66 days.

(21) Appl. No.: 17/494,751

(22) Filed: Oct. 5, 2021

(65) Prior Publication Data
US 2022/0249346 A1   Aug. 11, 2022

Related U.S. Application Data

(63) Continuation of application No. 14/868,259, filed on Sep. 28, 2015, now abandoned, which is a
(Continued)

(30) Foreign Application Priority Data

Mar. 28, 2013   (DE) .......................... 102013005361.7

(51) Int. Cl.
  *A61K 8/60*   (2006.01)
  *A61K 31/7115*   (2006.01)
(Continued)

(52) U.S. Cl.
  CPC .......... *A61K 8/606* (2013.01); *A61K 31/7115* (2013.01); *A61K 48/005* (2013.01); *A61Q 19/08* (2013.01); *C07K 14/78* (2013.01)

(58) Field of Classification Search
  CPC .. A61K 8/606; A61K 31/7115; A61K 48/005; C07K 14/78
  See application file for complete search history.

(56) References Cited

U.S. PATENT DOCUMENTS 7,074,596 B2    7/2006  Darzynkiewicz
8,288,347 B2 *  10/2012  Collette ............... A61K 31/167
                                                424/484
(Continued)

FOREIGN PATENT DOCUMENTS

WO   WO-2007024708 A2 *  3/2007  .......... A61K 38/177
WO      2008052770 A2     5/2008
(Continued)

OTHER PUBLICATIONS

AMA Style Insider (Sep. 2012) downloaded from Around, About, Approximately | AMA Style Insider on May 9, 2023.*
(Continued)

*Primary Examiner* — Terra C Gibbs

(57) ABSTRACT

The invention relates to a polyribonucleotide, a cosmetic and pharmaceutical compound that has the polyribonucleotide and a medicinal product that has the polyribonucleotide and the compound.

18 Claims, 6 Drawing Sheets

Specification includes a Sequence Listing.

Related U.S. Application Data continuation of application No. PCT/EP2014/056233, filed on Mar. 27, 2014.

(51) Int. Cl.
 A61K 48/00 (2006.01)
 A61Q 19/08 (2006.01)
 C07K 14/78 (2006.01)

(56) References Cited

U.S. PATENT DOCUMENTS

| | | | |
|---|---|---|---|
| 2009/0093433 | A1 | 4/2009 | Woolf et al. |
| 2012/0195936 | A1 | 8/2012 | Rudolph et al. |
| 2012/0251618 | A1 | 10/2012 | Schrum et al. |

FOREIGN PATENT DOCUMENTS

| | | | |
|---|---|---|---|
| WO | 2008067195 | A2 | 6/2008 |
| WO | 2008100789 | A2 | 8/2008 |
| WO | 2009127230 | A1 | 10/2009 |
| WO | 2011008904 | A1 | 1/2011 |
| WO | 2011012316 | A2 | 2/2011 |
| WO | 2012019168 | A2 | 2/2012 |
| WO | 2012045075 | A1 | 4/2012 |
| WO | 2012045082 | A2 | 4/2012 |
| WO | 2012135805 | A2 | 10/2012 |
| WO | 2012158736 | A1 | 11/2012 |
| WO | 2014154844 | A1 | 10/2014 |

OTHER PUBLICATIONS

E.insights (Jun. 2014) downloaded from https://www.editage.com/insights/scientific-writing-difference-in-meaning-of-about-around-and-approximately on May 9, 2023.*
Kormann et al. (Nature Biotechnology, 2011 vol. 29:154-157).*
GenBank Accession No. BC035570 (Mar. 4, 2003).*
Prabhakar et al. (Journal of Drug Delivery & Therapeutics; 2013, 3:213-221).*
Warren et al. (Cell Stem Cell, 2010 vol. 7:618-630).*
Non-Final Rejection for U.S. Appl. No. 14/868,259, dated Jan. 31, 2017, 11 pages.
Amendment in Response to Non-Final Office Action under 37 C.F.R. 1.111 for U.S. Appl. No. 14/868,259, dated Jun. 30, 2017, 15 pages.
Final Rejection for for U.S. Appl. No. 14/868,259, dated Oct. 12, 2017, 18 pages.
Application Initiated Interview Summary for U.S. Appl. No. 14/868,259, dated Feb. 26, 2018, 3 pages.
Application Summary of Interview with Examiner for U.S. Appl. No. 14/868,259, dated Feb. 27, 2018, 2 pages.
Request Continue Exam and Amendment in Response to FOA under 37 C.F.R. 1.116 for U.S. Appl. No. 14/868,259, dated Apr. 10, 2018, 18 pages.
Affidavit-Traversing Rejections or Objections Rule 132 for U.S. Appl. No. 14/868,259, dated Apr. 10, 2018, 6 pages.
Non-Final Rejection for U.S. Appl. No. 14/868,259, dated Apr. 26, 2018, 20 pages.
Amendment in Response to Final Office Action under 37 C.F.R. 1.111 for U.S. Appl. No. 14/868,259, dated Sep. 25, 2018, 18 pages.
Final Rejection for U.S. Appl. No. 14/868,259, dated Dec. 27, 2018, 19 pages.
Amendment in Response to Final Office Action under 37 C.F.R. 1.116 for U.S. Appl. No. 14/868,259, dated Jun. 26, 2019, 10 pages.
Non-Final Rejection for U.S. Appl. No. 14/868,259, dated Aug. 13, 2018, 14 pages.
Amendment in Response to Non-Final Office Action under 37 C.F.R. 1.111 for U.S. Appl. No. 14/868,259, dated Jan. 13, 2020, 10 pages.
Final Rejection for U.S. Appl. No. 14/868,259, dated Feb. 27, 2020, 12 pages.
Amendment in Response to Final Office Action under 37 C.F.R. 1.116 for U.S. Appl. No. 14/868,259, dated Jun. 26, 2020, 20 pages.
Non-Final Rejection for U.S. Appl. No. 14/868,259, dated Aug. 11, 2020, 19 pages.
Response to Non-Final Action under 37 C.F.R. 1.111 for U.S. Appl. No. 14/868,259, dated Feb. 8, 2021, 28 pages.
Final Rejection for U.S. Appl. No. 14/868,259, dated May 5, 2021, 21 pages.
Abandonment for U.S. Appl. No. 14/868,259, dated Nov. 15, 2021, 2 pages.
AMA Style Insider. Around, About, Approximately. Downloaded on Oct. 4, 2017 from http://amastyleinsider.com/2012/09/14/around-about-approximately/.
David Wolman. Natural Healing. (MIT Technology Reviews, Biomedicine, Jun. 21, 2005), pp. 1-6, downloaded from https://www.technologyreview.com/s/404312/natural-healing/ on Jan. 26, 2017.
GenBank Accession No. BC035570, Submitted (Jul. 31, 2002) National Institutes of Health, Mammalian Institute, 31 Center Drive, Room 11 A03, Bethesda, MD 20892-2590, USA.
Hirano et al. "Functional rescue of elastin insufficiency in mice by the human elastin gene: implications for mouse models of human disease," Circulation Research (2007) 101:523-531.
International Search Report and Written Opinion for PCT/EP2014/056233, dated Jul. 14, 2014, 32 pages.
Internet Search HGNC ID: HHGNC 3327. Retrieved from http://www.genenames.org/cgibin/gene_symbol_report?hgnc_id=HGNC:3327 Retrieved in 2013.
Kormann et al. "Expression of therapeutic proteins after delivery of chemically mRNA in mice," Nature Biotechnology (2011) 29(2):154-159.
Mandal et al. "Reprogramming human fibroblasts to pluripotency using modified mRNA," Nature Protocols (2013) 8:568-582.
NCBI—Elastin isoform protein sequence. Downloaded from https://www.ncbi.nlm.nih.gov/protein/126352440 on Apr. 12, 2018.
Nolte et al. (Mol. Med. 2011 vol. 17:1213-1222).
Scientific writing: Difference in meaning of "About," "Around," and "Approximately" by Yateendra Joshi. Jun. 12, 2014. Downloaded from https ://www. editag.com/insights/scientific-writing-difference-in-meaning-of-about-around-and-approximately?regid=1507142317 on Oct. 4, 2017.
Warren et al. "Highly efficient reprogramming to pluripotency and directed differentiation of human cells with synthetic modified mRNA," Cell Stem Cell (2010) 7:618-630.
Xiong et al., "Elastic fibers reconstructed using adenovirus-mediated expression of tropoelastin and tested in the elastase model of abdominal aortic aneurysm in rate," J Vasc Surg (2008) 48(4):965-973.

* cited by examiner

STABILIZED POLYRIBONUCLEOTIDE CODING FOR AN ELASTIC FIBROUS PROTEIN

CROSS-REFERENCES TO RELATED APPLICATIONS

This application is a continuation of U.S. patent application Ser. No. 14/868,259, now pending, which is a continuation of international patent application PCT/EP2014/056233 filed on 27 Mar. 2014 and designating the U.S., which has been published in German, and claims priority from the German patent application DE 10 2013 005 361.7, filed on 28 Mar. 2013. The entire contents of these priority applications are incorporated herein by reference in their entireties for all purposes.

REFERENCE TO A SEQUENCE LISTING

This application contains references to nucleic acid sequences and/or amino acid sequences which have been submitted concurrently herewith as the sequence listing text file "4567-2012502_20211130_SeqList_ST25.txt", date recorded: Nov. 30, 2021, size: 58,290 bytes). The aforementioned sequence listing is hereby incorporated by reference in its entirety pursuant to 37 C.F.R. § 1.52 (e) (5).

FIELD

The present invention relates to a polyribonucleotide, a cosmetic and pharmaceutical composition comprising said polyribonucleotide, and a medical product comprising said polyribonucleotide or said composition.

BACKGROUND

Elastic fibers are the largest structures of the extracellular matrix. They give elastic properties to the tissue. The elastic fibers consist of two morphologically distinct components. The first and largest component of the mature fiber is the elastin. The second component are the micro-fibrils which mainly consist of fibrillin and are associated with further proteins such as the micro-fibrills associated glycoproteins (MAGPs), fibulines, and the elastin-micro-fibrills-interface localized proteins (EMILIN). The lysyl oxidase (LOX) is involved in the cross-linking of the elastic fibers.

Elastin and its soluble precursor tropoelastin belong to the major structural proteins of the body. It provides structure and support to the connective tissue and is responsible for the elasticity of arteries and the lung.

Elastin is encoded by the ELN gene. Mutations in the ELN gene may result in inherited disorders such as dermatochalasis, Williams-Beuren syndrome, and sub valvular innate aortic stenosis (SVAS).

Arteriosclerotic blood vessels are subject to a loss of elastin which cannot be naturally compensated by cells involved in the regeneration. This is due to the fact that elastin-forming cells only synthesize and secrete new elastin up to a certain age and during the growth of the organism. In the following the protein is cross-linked in the extracellular space with each other and with other proteins of the connective tissue. Since elastin is particularly durable because of the cross-linking after having reached the full body height the need of an organism is fulfilled and the synthesis is almost ceased.

Because of the reduced synthesis of elastin in the old age the skin loses its flexibility and begins to develop wrinkles.

There are no satisfying or even causal therapies of a deficient synthesis of elastic fibrous protein, in particular elastin.

Hirano et al. (2007), Functional rescue of elastin insufficiency in mice by the human elastin gene: implications for mouse models of human disease, Circulation Research 101: 523-531, describe the introduction of human elastin by means of a DNA plasmid into mice oocytes. However, this approach is not suitable for a therapeutic application in humans.

SUMMARY

Against this background it is an object of the present invention to provide a substance by means of which the problems mentioned at the outset can be solved. In particular, such a substance should be provided which can counteract a lack of elastic fibers or elastic fibrous protein, respectively, and which can stimulate the synthesis of elastic fibers or elastic fibrous protein.

This object is achieved by the provision of a polyribonucleotide encoding an elastic fibrous protein comprising a nucleotide sequence which comprises at least one chemical modification stabilizing said polyribonucleotide.

The inventors have surprisingly realized that a deficiency of the synthesis of elastic fibrous protein can be counteracted in a causal manner by providing the coding sequence to the cell in a form ready for a direct translation. The polyribonucleotide according to the invention can be introduced into the cells to be regenerated and can induce the synthesis of elastic fibrous protein in situ. The cells transfer the synthesized elastic fibrous protein into the natural path of the assembly of elastic fibers. This ensures not only the synthesis of the elastic fibrous protein but also the new synthesis of the elastic fibers. Neither the administration of elastic proteins as such nor of other proteins being involved in the genesis of elastic fibers could so far provide similar results.

The stabilization of polyribonucleotides, for example of mRNA, is extensively described in the state of the art. It is referred to the following publications: US 2009/0093433, WO 2011/012316, WO 2012/135805, WO 2012/045082, WO 2012/019168, WO 2012/045075, WO 2012/158736. Furthermore, the stabilization of mRNA by chemical modification of ribonucleotides is described in the publications of Warren et al. (2010), High efficient reprogramming to pluripotency and directed differentiation of human cells with synthetic modified mRNA, Cell Stem Cell 7, p. 618 to 630, and Kormann et al. (2011), Expression of therapeutic proteins after delivery of chemically modified mRNA in mice, Nature Biotechnology, Vol. 29, No. 2, p. 154 to 159, Mandal and Rossi (2013), Reprogramming human fibroblast to pluripotency using modified mRNA, Nature Protocols, Vol. 8, No. 3, p. 568 to 582.

Methods for the synthesis of polyribonucleotides, such as mRNA, are extensive described in the state of the art. One of the suitable methods is the in vitro transcription (IVT). The resulting mRNA is also referred to as IVT-mRNA.

The inventors have realized that the synthesis of elastic fibrous protein in situ, that means in the cell, can compensate a deficiency, e.g. due to a mutation but also due to an age-related cease of the natural synthesis, in a targeted manner.

Because of the chemical modification the polyribonucleotide is sufficiently stable to be translated by the cell-own machinery. However, the polyribonucleotide according to the invention is sufficiently instable to only develop a temporary effect so that side effects can be largely avoided.

As the inventors were able to show, the immune response of an organism treated with the polynucleotide according to the invention is sufficiently smaller than by using a reference polyribonucleotide which is not chemically modified. This results in an additional increase in the therapeutic benefit of the polyribonucleotide according to the invention.

The object underlying the invention is herewith completely solved.

According to the invention it is preferred if the elastic fibrous protein is selected from the group consisting of: elastin/tropoelastin, fibrillin, micro-fibrills associated glycoprotein (MAGP), fibuline, elastin-micro-fibrills-interface localized protein (EMILIN) and lysyl oxidase (LOX) and precursors thereof.

This measure has the advantage that the polyribonucleotide according to the invention is configured for the induction of the in situ synthesis of the most important elastic fibrous proteins. For the mentioned elastic fibrous proteins preference is given to the human variants so that the use in humans is fostered.

In an embodiment the polyribonucleotide is an mRNA.

This measure has the advantage that the polyribonucleotide is provided in a form which can immediately be used by the cell-own protein synthesis machinery. This may include e.g. an in vitro transcribed mRNA (IVT-mRNA).

According to the invention one of the following mRNA stabilized by chemical modification is preferred: human elastin, transcript variant 1 (cDNA, NCBI data base NM_000501.2; SEQ ID No. 2), transcript variant 2 (cDNA, NCBI data base NM_001081752.1; SEQ ID No. 3), transcript variant 3 (cDNA; NCBI data base NM_001081753.1; SEQ ID No. 4), transcript variant 4 (cDNA, NCBI data base NM_001081754.1; SEQ ID No. 5), transcript variant 5 (cDNA, NCBI data base NM_001081755.1; SEQ ID No. 6).

In another embodiment the at least one chemical modification stabilizing said polyribonucleotide comprises a chemically modified nucleoside, preferably a modified uridine and/or cytidine.

By this measure the inventors have made use of the findings which are e.g. described by Kormann et al. (I.c.), namely that the mRNA after a chemical modification of the uridine ribonucleotides and/or cytidine ribonucleotides is not so easily recognized by structures of the immune system, such as the signal transduction mediating PRRs ("pattern recognition receptors") or "Toll-like receptors", thereby activating a significantly weakened immune response and obtaining a longer half-life period.

According to the invention a nucleoside also encompasses a corresponding nucleotide comprising in comparison to the nucleoside additional phosphate residues.

The following chemically modified uridines or uridine ribonucleotides are of particular suitability: pseudouridine, 2-thiouridine, 5-methyluridine, 5-methyluridine-5'-triphosphate (m5U), 5-idouridine-5'-triphosphate (I5U), 4-thiouridine-5'-triphosphate (S4U), 5-bromouridine-5'-triphosphate (Br5U), 2'-methyl-2'-deoxyuridine-5'-triphosphate (U2'm), 2'-amino-2'-deoxyuridine-5'-triphosphate (U2'NH2), 2'-azido-2'-deoxyuridine-5'-triphosphate (U2'N3), 2'-fluoro-2'-deoxyuridine-5'-triphosphate (U2'F) and combinations thereof.

Especially suitable chemically modified cytidines or cytidine ribonucleotides are: 5-methylcytidine, 3-methylcytidine, 2-thiocytidine, 2'-methyl-2'-deoxcytidin-5'-triphosphate (C2'm), 2'-amino-2'-deoxycytidine-5'-triphosphate (C2'NH2), 2'-fluoro-2'-deoxycytidine-5'-triphosphate (C2'F), 5-iodcytidine-5'-triphosphate (I5U), 5-bromocytidine-5'-triphosphate (Br5U), 2'-azido-2'-deoxycytidine-5'-triphosphate (C2'N3) and combinations thereof.

According to the invention at least approx. 5%, further preferably at least approx. 7.5%, further preferably at least approx. 10%, and highly preferably at least 25% of the nucleosides or uridines and/or cytidines are modified.

Even though at least approx. 50% or approx. 100% of the nucleosides or uridines and/or cytidines can be modified the inventors have realized that a modification of up to approx. 25% of the nucleosides is sufficient for a stabilization of the polyribonucleotide according to the invention and reduction of the immune response. This has the advantage that the costs for the preparation of the polyribonucleotide according to the invention are significantly lower than for a 100% modification.

In another embodiment the chemical modification is selected from the group consisting of: 5' cap structure, preferably a 5' guanine cap, poly (A) tail, a cap structure analog [anti-reverse cap analog (ARCA; 3'O-Me-m$^7$G(5') ppp(5')ppp(5')G)], a strengthening of the translation-initiation sequence at the start codon AUG, e.g. by the sequence (CCCCGC)aucGagAUG.

By this measure an additional stabilization of the polyribonucleotide according to the invention is achieved in a beneficial manner.

In another embodiment the polyribonucleotide according to the invention comprises the sequence of SEQ ID No. 1, where at least approx. 5%, further preferably at least approx. 7.5%, further preferably at least approx. 10%, and highly preferably at least approx. 25% of the uridines, and/or where at least approx. 5%, further preferably at least approx. 7.5%, further preferably at least approx. 10%, and highly preferably at least approx. 25% of the cytidines are chemically modified.

As mentioned above it is true that also at least approx. 50% or at least approx. 100% of the nucleosides can be modified, however an approx. 25% modification is sufficient.

The definition of "chemically modified" as set forth above applies here correspondingly. Preferably an exchange of uridine (U) against pseudouridine or pseudouridinetriphosphate (ΨFUTP) and/or of cytidine (C) against 5-methylcytidine or 5-methylcytidinetriphosphate (mCTP) takes place.

The polyribonucleotide according to the invention preferably encodes an amino acid sequence which is selected from the group consisting of: SEQ ID No. 7, SEQ ID No. 8, SEQ ID No. 9, SEQ ID No. 10, and SEQ ID No. 11.

This measure has the advantage that the polynucleotide according to the invention encodes one of the different isoforms of elastin (SEQ ID No. 7: isoform a, NCBI data base NP_00049.2; SEQ ID No. 8: isoform b, NCBI data base NP_001075221.1; SEQ ID No. 9: isoform c, NCBI data base NP_001075222.1; SEQ ID No. 10: isoform d, NCBI data base NP_001075223.1; SEQ ID No. 11: isoform e, NCBI data base NP_001075224.1). The elastin isoforms comprise the effect which has been realized by the invention.

According to the invention it is preferred if the polyribonucleotide is configured for the induction of the synthesis of elastic fibrous proteins, in particular in age-related loss of elasticity of the skin (wrinkle formation), promotion of the wound healing, for the treatment of a deficient synthesis of elastic fibrous proteins, or for the treatment of a disease selected from the group consisting of: arteriosclerosis, aortic stenosis, aortic aneurysm, pulmonary emphysema, dermatochalasis, Williams-Beuren syndrome, sub valvular innate aortic stenosis (SVAS).

In addition, by means of the polyribonucleotide according to the invention the vaginal tissue can be treated, e.g. following a pregnancy, for the stimulation of the elastin synthesis and the recovery of the elasticity.

Furthermore, the polyribonucleotide according to the invention can be configured for dental applications, for example for the reconstruction and/or regeneration of soft or hard tissues of the periodontium. For this reason the polyribonucleotide according to the invention is preferably provided or configured for a transdermal application.

These measures have the advantage that the polyribonucleotide according to the invention is configured for the treatment of important diseases and phenomena which may result from a reduced synthesis of elastic fibrous protein.

For this reason the invention relates to the use of the polyribonucleotide according to the invention for the before-mentioned purposes.

Furthermore, the invention relates a method for the induction of the synthesis of elastic fibrous protein, in particular for the before-mentioned purposes, comprising the following steps: (1) provision of the polyribonucleotide according to the invention, if applicable, in a pharmaceutically/cosmetically acceptable formulation, and (2) administration of the polyribonucleotides in or to an organism.

The application of the polyribonucleotide in or to an organism may be effected via a topical application, for example onto the skin of the organism, preferably the human skin. For this purpose the polynucleotide may be a component of a dermatological dosage form such as a cream, lotion, ointment etc. However, the administration can also be effected via appropriate dosage forms systemically, orally, intravenously, intraarterially, intramuscularly, intrathecally, subcutaneously, intraperitoneally, intracardially, intravitreally, or intraosseously etc.

The transdermal administration of the polynucleotide according to the invention can be effected by means of micro needles, nanopatches, nanoparticles or by means of a gene gun. In addition, active systems are appropriate which use iontophoresis. Here a very small electrical current is transferred through the skin, which carries charged molecules. An example for this is the iontophoresis LTS-TTS system of the company LTS Lohmann Therapie-Systeme AG, Andernach, Germany.

Against this background a further object of the present invention is a composition comprising the polyribonucleotide according to the invention. The composition according to the invention may be a cosmetical and/or pharmaceutical composition comprising a cosmetically or pharmaceutically acceptable formulation. Cosmetically and pharmaceutically acceptable formulations are generally known in the state of the art. They are e.g. described in the assay of Kibbe et al., *Handbook of Pharmaceutical Excipients*, 5. Edition (2006), American Pharmaceutical Association. The compositions may be configured as a mono preparation which contains the polyribonucleotide as the only active agent. However, they may contain additives and, if applicable, further active agents and excipients which are beneficial for the uses according to the invention, including transfection tools such as liposomes, hydro gels, kationic polymers or peptides, salts, binding agents, solvents, dispersing agents and further compounds which are commonly used in connection with the formulation of cosmetics and pharmaceuticals.

In another embodiment of the invention the composition can additionally comprise an immuno suppressive agent, preferably an interferon inhibitor.

This measure has the advantage that due to the chemical modification the already reduced immune response of a host treated with the polyribonucleotide according to the invention is further reduced. The suppression of the immune response after the administration of a therapeutic mRNA by the use of the interferon inhibitor B18R which is suited for the use according to the invention, is documented in the state of the art, for example in Warren et al. (l.c.).

Another subject-matter of the present invention is a medical product, for example a patch or implant, which comprises the polyribonucleotide according to the invention or the composition according to the invention, respectively, or which is coated with the latter. The implant may be a medical implant, preferably a stent including a coronary stent, or vascular implant, stent graft or a bone implant.

The implant allows a targeted treatment of arteriosclerotic blood vessels and/or local tissue areas, such as vaginal tissues, soft and hard tissues of the periodontium for the recovery of the elasticity.

Another subject-matter of the present invention is a wound dressing coated with the polyribonucleotide according to the invention.

Such a wound dressing can reduce the scaring and maintain the elasticity of the scar tissue by the induction of elastin synthesis.

It is to be understood that the features of the invention mentioned above and those yet to be explained below can be used not only in the respective combination indicated, but also in other combinations or in isolation, without leaving the scope of the present invention.

The present invention is now further explained by means of embodiments which result in further characteristics and advantages of the invention. The examples are purely illustrative and do not restrict the scope of the invention. Reference is made to the enclosed figures.

EXAMPLES

1. Plasmids Constructs for the RNA Synthesis

An elastin, transcript variant 1 encoding (SEQ ID No. 2) Sp6-promoter containing plasmid, pCMV-Sp6_ELN, cloned into *E. coli*, was purchased from Thermo Scientific.

The Luciferase encoding, T7-promoter containing plasmid, pCMV-GLuc-1 used as a reporter gene, was purchased from Nanolight Technology, Inc. and cloned into Qiagen EZ competent *E. coli* from the Qiagen PCT cloning kit.

The plasmids contain sites for sequencing with primers such as the M13 forward and reverse primers, and promoter regions for polymerases, such as Sp6 and T7. These sequences can be found 5' or 3' to the inserted sequence of interest, respectively. Additionally, the insert region is flanked by short recognition sequences for specific restriction enzymes.

2. Verification of Plasmid Inserts

The plasmids were isolated with the Qiagen Plasmid Maxi kit (Qiagen).

Figure 1:
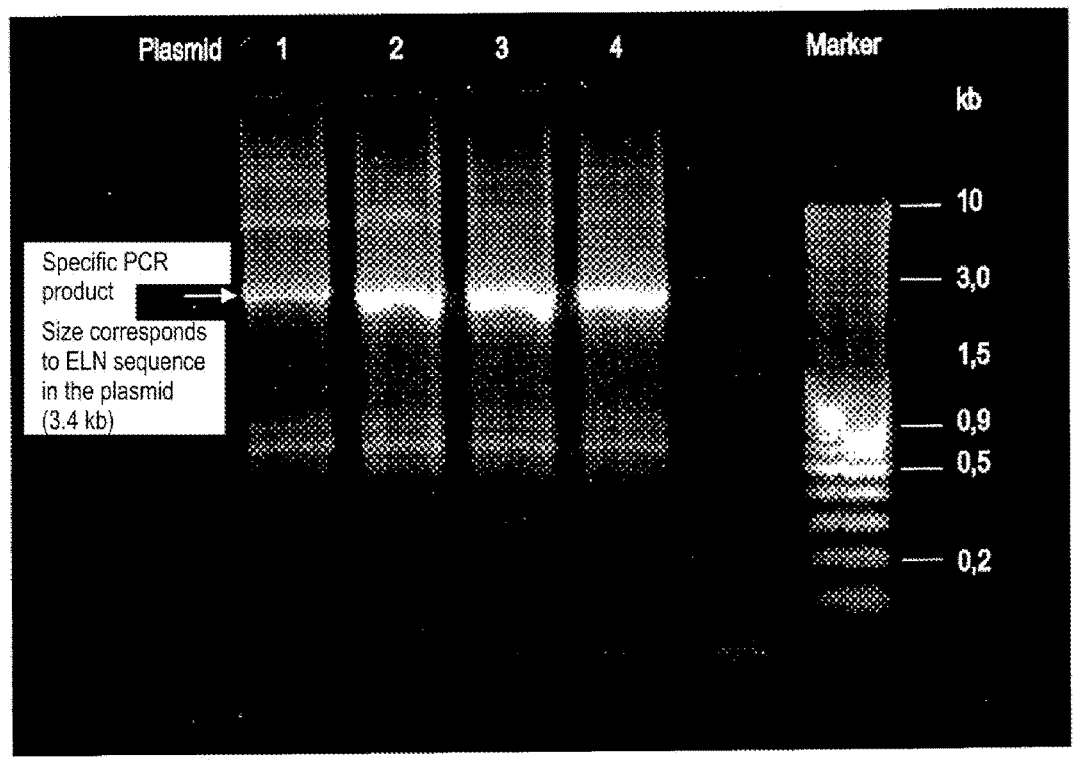
FIG. 1: Plasmid preparations of four individually selected bacteria colonies were tested for correct insert by means of ELN-specific PCR. Detection of PCR products by means of agarose gel electrophoresis, 1.2% (120 V, 30 min). PCR cycles: denaturating 3 min, 94° C., 1. 40 sec, 94° C.-2. 1 min, 58° C.-3. 2.5 min, 72° C.; final amplification: 7 min, 72° C.

Insert-specific primers were designed with a free primer designing tool from NCBI and produced by Eurofins MWG Operon. The plasmid inserts were verified by PCR with the insert-specific primer pairs (FIG. 1), and the following cycling parameters were used: denature 3 min at 94° C.; 1. 40 sec at 94° C.; 2. 1 min at 58° C.; 3. 2.5 min at 72° C.; repeat steps 1-3, 28×; final amplification 7 min, 72° C.

Additionally, plasmid inserts were sequenced completely through the company GATC Biotech with self-designed insert-specific primers and with M13-forward and reverse primers. The sequence assembly was done with the DNA-baser program.

Figure 2:
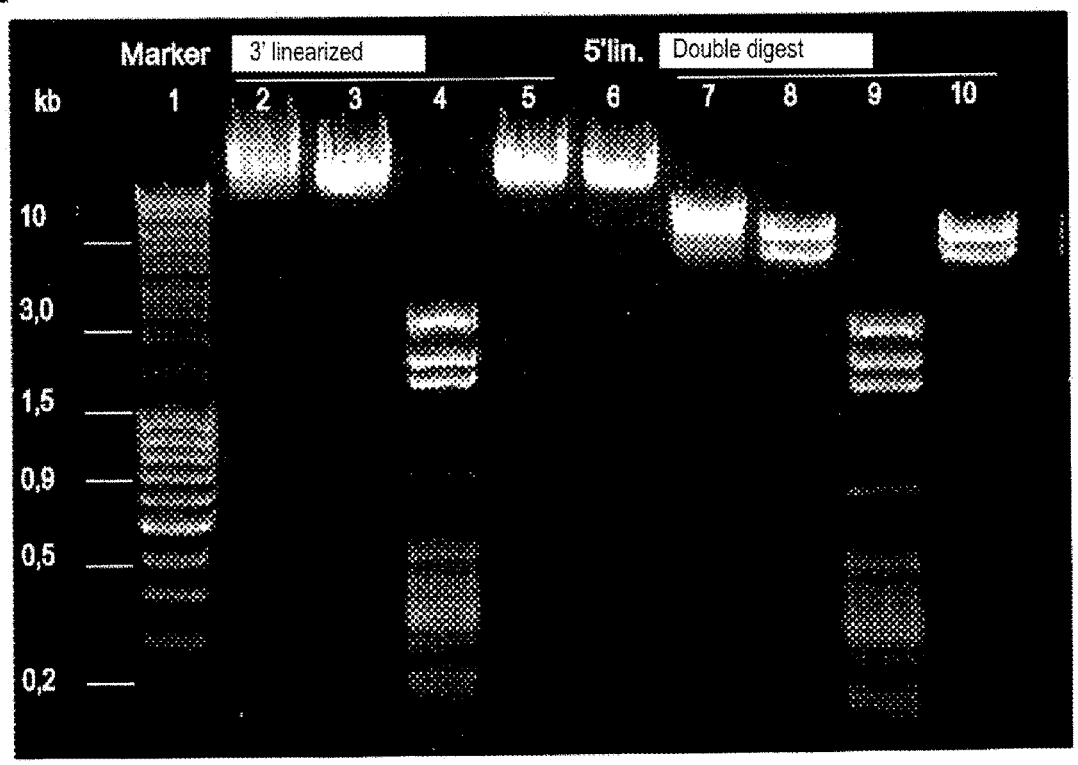
FIG. 2: Distinctively cutting restriction enzymes were determined by means of test digests of the plasmid and analysis in the following on a 1% agarose gel (120 V, 40 min). Bands: 1-marker/DNA ladder, 2-5: test digest of the plasmid with different downstream (3') cutting restriction enzymes: 2: Not I, 3: Xba I, 4: Bfa I, 5: Xho I, 6: digest with downstream (5') cutting enzyme, EcoRI, 7-10: downstream cutting enzymes were combined with Ecor I (double digest), order as 2-5. kb=kilobases.

3. In Vitro Synthesis of ELN-mRNA with Different Amounts of Modified Nucleic Acids For the in vitro transcription (IVT) plasmids were linearized downstream of the gene of interest with the Fast Digest Enzyme System (Fermentas/Thermo Scientific) and purified with the MiniElute PCR clean up kit (Qiagen). Test digests were performed prior to the experiment (FIG. 2).

The in vitro transcription was performed according to the manufacturer's instructions with MEGAscript Sp6 kit. For each 40 μL IVT reaction 1 μg of linearized template was used. To optimize the stability and cytocompatibility of IVT-mRNAs in the reactions different ratios of the nucleic acid triphosphates 5-methylcytidine and pseudouridine (Tri-Link Biotechnologies) were combined with standard nucleotides from the kit.

TABLE 1 nucleotide mixtures in the IVT reactions with different amounts of 5-methylcytidine and pseudouridine

| | CTP | 5-methylcitidine | UTP | Pseudouridine |
|---|---|---|---|---|
| 25% modification | 5.25 mM | 1.75 mM | 5.25 mM | 1.75 mM |
| 50% modification | 3.5 mM | 3.5 mM | 3.5 mM | 3.5 mM |
| 100% modification | — | 7 mM | — | 7 mM |

In each IVT reaction 6 mM ATP, 3 mM GTP (from the kit) and 2 mM 3'-O-Me-m$^7$G(5')ppp(5')G (anti-reverse cap-analog from New England Biolabs) were used. Further components were added as indicated in the manual of the kit.

The reactions were incubated for 3.5 hours at 37° C. and treated with DNase I from the kit at the end of the incubation period in compliance with the instructions of the manufacturer, in order to eliminate the template DNA.

The polyadenylation was made with the PolyA Tailing kit (Ambion) according to the instructions of the manufacturer.

Figure 3:
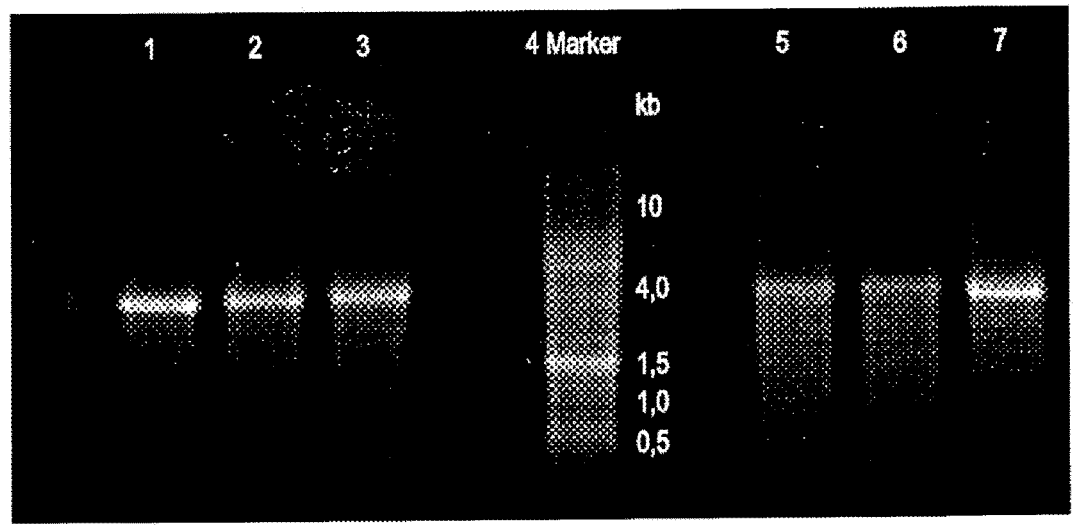
FIG. 3: In vitro synthesized ELN-mRNA in denaturating agarose gel electrophoresis 1% (16% formaldehyde, 100 V, 45 min). 1: IVT reaction after 3 h incubation; 2: IVT reaction with polyadenylating mix and 25 min incubation; 3: as in 2, after 45 min; 4: marker; 5-6: purified, polyadenylated ELN-mRNAs; 5, 6: with Ambion MEGAclear Kit (catalog number AM1908); 7: with Qiagen RNeasy Midi Kit, double RNA amount (catalog number: 75142)

The mRNA was purified with the RNeasy mini kit (Qiagen). The detection of the elastin mRNA was made by denaturating agarose gel electrophoresis (FIG. 3). The concentrations of mRNAs were measured by means of BioPhotometer6131 (Eppendorf).

4. In Vitro Translation of In Vitro Transcribed mRNAs

The quality of the in vitro transcribed mRNA was determined indirectly by in vitro translation with the Retic Lysate kit (Ambion), following luminescence measurement for the Luciferase or western blot analysis for elastin. The in vitro translation reactions were set up according to the instructions of the manufacturer.

5. Cell Lines and Chemicals Used for the Transfection of IVT-mRNAs

The lung carcinoma cell lines A549 and SK-MES were used for the first trials. The endothelial cell/A549-hybridoma cell line EA-hy926 was used to establish effective transfection methods for endothelial cells and tissues.

All m RNA transfections were performed by using the transfection reagent Lipofectamine2000 (Invitrogen/Life Technologies). The medium for transfections was OptiMEM (Gibco/Life Technologies). The negative controls throughout all experiments were OptiMEM with equal amounts of Lipofectamine2000 used for mRNA transfections or mRNA without transfection reagent in OptiMEM.

6. Transfection of IVT-mRNAs in Cell Culture

For the transfections with elastin mRNA the cells were plated with a density of 500,000 cells per well in 6-well plates one day prior to the experiments.

The transfection was made with 5 or 10 μg of elastin mRNA and 3.3 μL of transfection reagent per well diluted in OptiMEM, based on the indications of the manufacturer.

The medium with the mRNA transfection complexes was added to the cells and the plates were incubated for 4 hours under cell culture conditions. Afterwards, ⅔ of the transfection mixes were replaced with fresh culture medium and the cells were incubated overnight. This transfection method was repeated for the following 2 days. At the third day the transfection complexes were completely replaced with fresh cell culture medium.

Medium and cells were analyzed by one day after the last transfection.

7. Expression of the Luciferase Reporter Gene In Vitro

The first assessment of the Luciferase expression was performed 5 hours after the transfection and then following every day until the expression declined. For luminescence measurements, representing the Luciferase expression, 20 μL medium was taken from each well 6/24/48/72 hours and 5/10/25 days after transfection, with medium change after each sample taking.

8. Measurement of the Luciferase Activity

Figure 4:
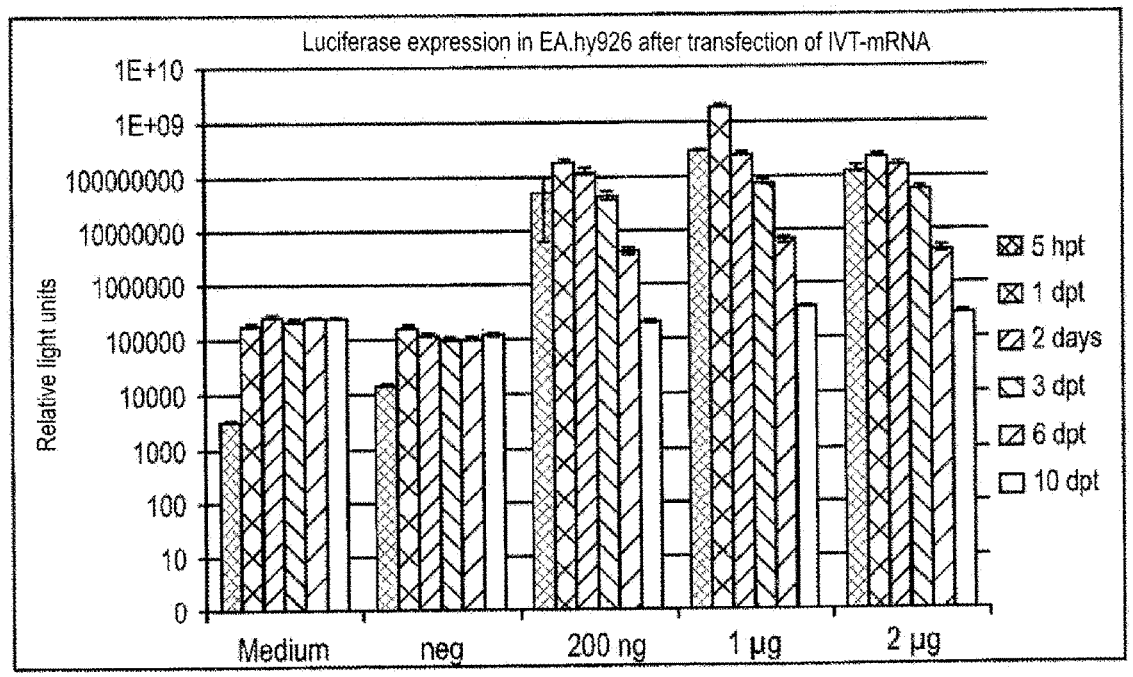
FIG. 4: Detection of reporter gene expression: detection of the Luciferase expression after transfection of IVT-Luciferase-mRNA into EA.hy926. hpt=hours post transfection; dpt=days post transfection.

The activity of the Luciferase enzyme directly after the in vitro translation or 5 hours to 30 days after the transfection of IVT-mRNA into the cells was assessed by adding 100 μL of 2.5 ng/μL substrate coelenterazin to 20 μL cell medium from transfected cells or in vitro translation reaction, respectively. The resulting luminescence of the probes was measured in a microplate reader (Mithras LB 940, Berthold Technologies). FIG. 4 shows the measured luminescence relating to the Luciferase expression in the medium of IVT-mRNA transfected EA.hy926 cells.

The results show that even a low amount of 200 ng of IVT Luciferase mRNA can induce a significant Luciferase expression even after a short incubation period of 5 hours. A high expression can be reached with 1 μg of IVT-mRNA up to 24 hours after the transfection, however the following expression course does not differ from the probes with lower amount of IVT-mRNA. Even another increase of the amount of transfected IVT-mRNA up to 2 μg does not result in a higher expression.

9. Detection of (Tropo-)Elastin by Western Blot

Figure 5:
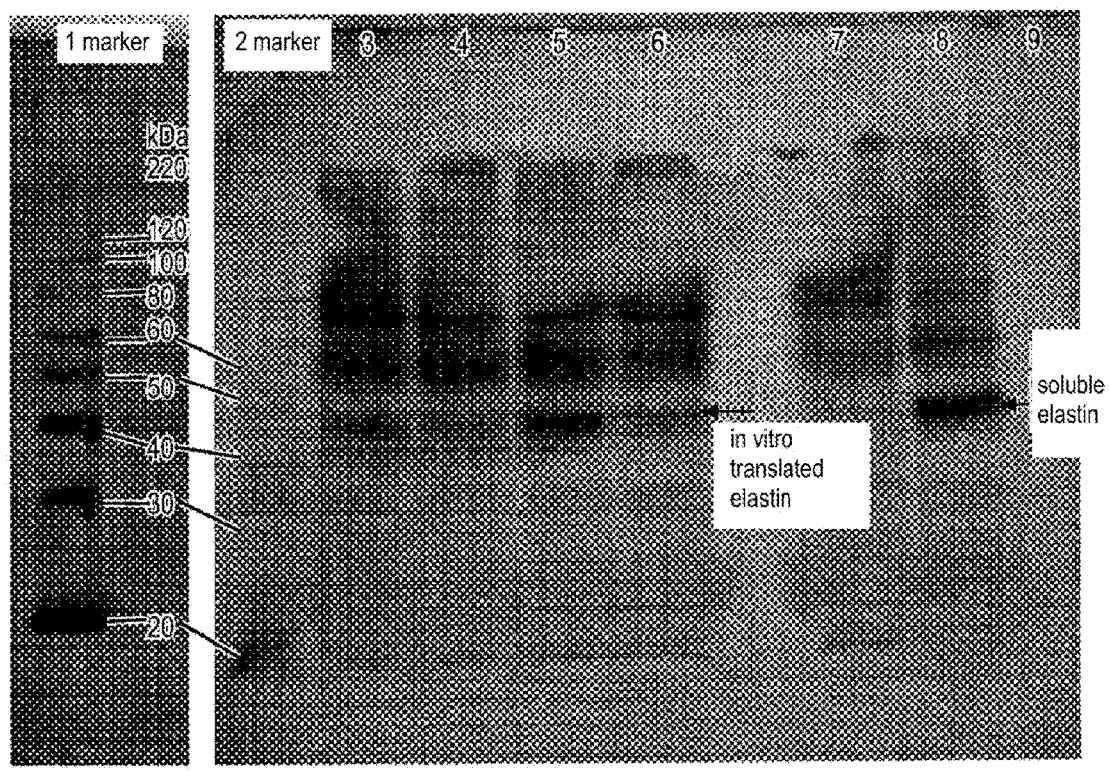
FIG. 5: In vitro synthesized ELN protein on the basis of four different in vitro synthesized ELN-mRNAs and controls: 1, 2: marker; 3-6: protein synthesis with ELN-mRNAs from different in vitro transcription reactions (5: mRNA with modified nucleotides); 7: in vitro translation reaction without mRNA (negative control); 8: as in 7, but with addition of human, soluble elastin protein from Calbiochem (catalog number: 324751) after incubation time; 9: only water solved elastin protein from Calbiochem—according to data sheet the protein should run as a smear band between 5 and 60 kDa. Native elastin protein is detected by means of the used antibody at a level of 50 kDa.

The proteins from the in vitro translation reactions were separated on a 8% SDS-PAGE and blotted on a nitrocellulose membrane for the immunodetection. The primary antibody was a rabbit polyclonal ELN antibody (central region) from Abgent and the secondary antibody was a goat anti-rabbit IgG (whole molecule) Alkaline Phosphatase Conjugate from Sigma-Aldrich. The elastin protein was revealed by precipitation of the indigo dye resulting from NBT/BCIP reaction with alkaline phosphatase (FIG. 5).

The detection of elastin after the in vitro translation made on the basis of IVT-elastin-mRNA confirms the integrity of the mRNA according to the invention. It is understood that a protein detection can only occur when the synthesized protein corresponds to the structures against which the antibody has been developed. For this reason the mRNA according to the invention must have been present in its entirety and functionality for the protein synthesis. Although there is apparently a non specific detection of proteins existing in the in vitro translation mix the specificity of the elastin band is unambiguous since it does not exist in the negative control which only contains the in vitro translation mix without IVT-mRNA.

10. Detection of the Expression of Tropoelastin in the Cell Culture

Figure 6:
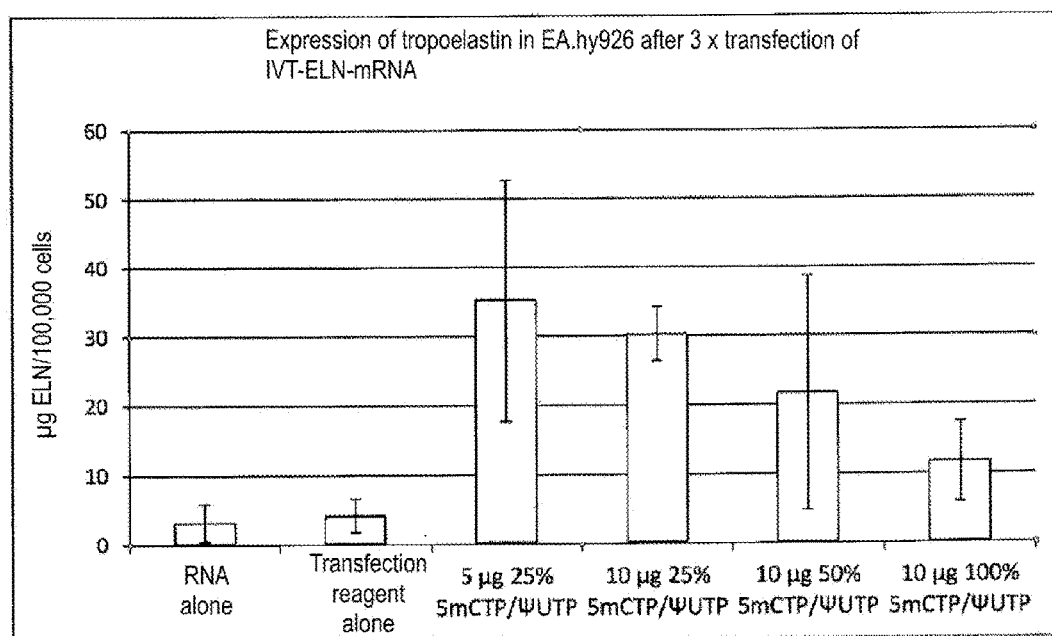
FIG. 6: Detection of the elastin expression by measuring the amount of tropoelastin in EA.hy926 cells after transfection at three successive days with IVT-ELN-mRNA; they contained different fractions of modified nucleic acids (mCTP/ΨUTP) and Lipofectamin2000. RNA or Lipofectamin2000 alone were used as negative controls.

The expression of elastin was analyzed with the Fastin™ Elastin Assay (Biocolor life science assays) according to the manufacturer's instructions. FIG. 6 shows the amount of tropoelastin isolated 24 hours after the last transfection with elastin-IVT-mRNAs, which contained various parts of modified nucleic acids.

After a 3-fold transfection of IVT-elastin-mRNA a significant expression of tropoelastin, i.e. of soluble and non cross-linked elastin, could be detected in the cells. It is clear that a particular large amount of 10 μg of transfected IVT-ELN-mRNA has no increasing effect on the elastin expression over only 5 μg. Also the higher amount of modified nucleotides has no positive influence on the expression. Therefore it seems that 5 μg of the IVT-ELN-mRNA with 25% of modified CTP/UTP can cause a sufficient detectable expression of elastin.

Figure 7:
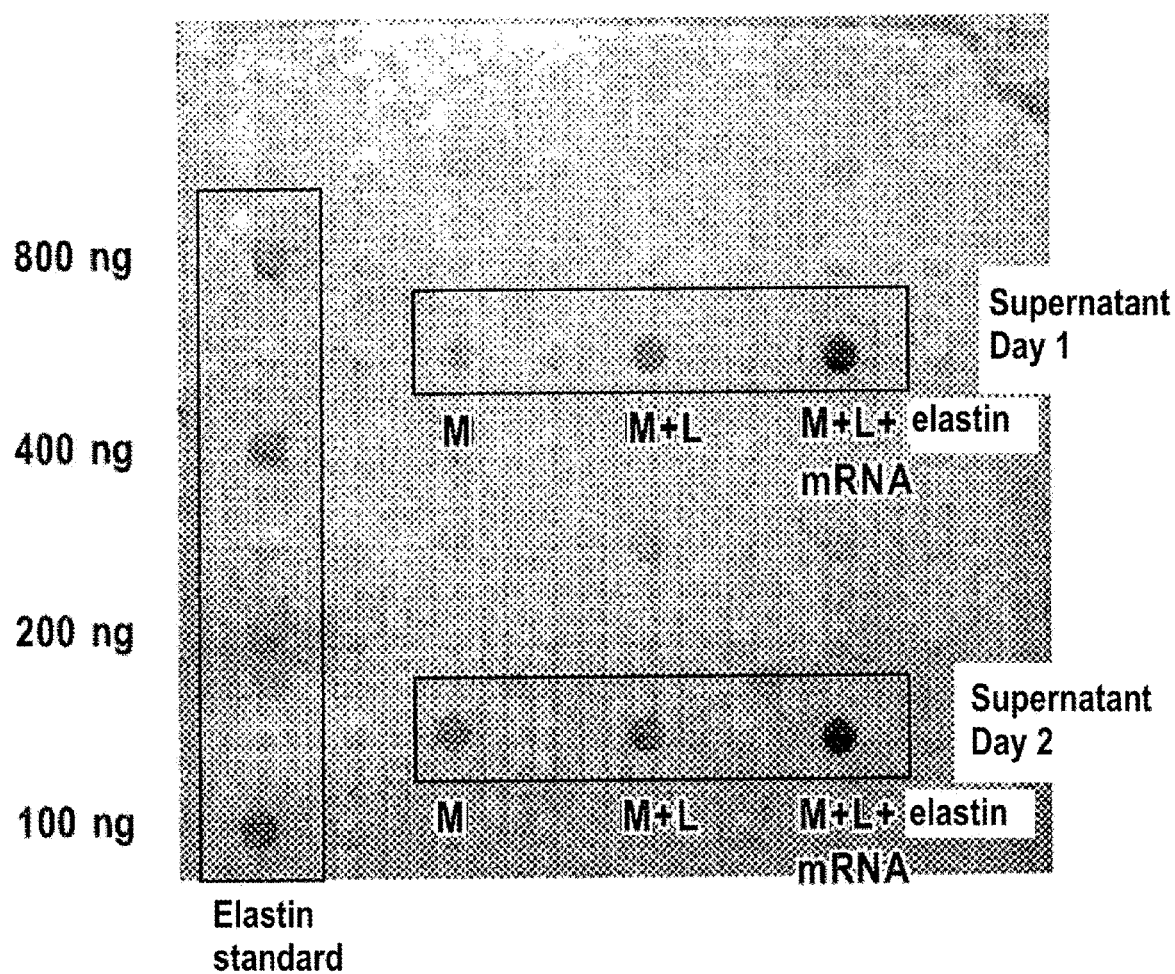
FIG. 7: Detection of the elastin expression in the supernatant of the EA.hy926 cells after transfection with 100% modified (mCTP/ΨUTP) IVT-ELN-mRNA by means of dot-blot assays; M: only cell culture medium, M+L: cell culture medium plus transfection reagent.

In another experiment $3\times10^5$ cells per well of a 6 well plate were seeded. At the following day the supernatants were aspirated and the cells were washed with 1 ml PBS. Then an incubation took place for 4 hours with Opti-MEM (M), Opti-MEM with Lipofectamine 2000 (M+L), and Opti-MEM with Lipofectamine 2000 and 2.5 μg of elastin-mRNA (100% 5mCTP/ΨUTP). The cell supernatants were collected after 24 and 48 hours. The supernatants were analyzed by means of dot-blot. The result is shown in FIG. 7. The detection of elastin was made by means of elastin-specific AB. The cells with elastin-mRNA-incubation (M+L+elastin mRNA) show a significantly stronger staining than the cells without mRNA-transfection (M, M+L). The EA.hy926-cells without elastin-mRNA synthesize low amounts of elastin, however by the elastin-mRNA-transfection the elastin synthesis is significantly increased.

11. Assessing the Immunogenicity of the IVT-mRNAs

Transfections for the analysis of cytokines and other markers of the immune activation were performed according to the mRNA-transfections described above. Additionally, the immunostimulant polyinosinic/polycytidylic acid (Sigma-Aldrich) was transfected at 100 ng/well as a positive control for cytokine activation. The cells were incubated with the transfection mix under cell culture conditions and the medium was replaced after 3 hours.

Figure 8:
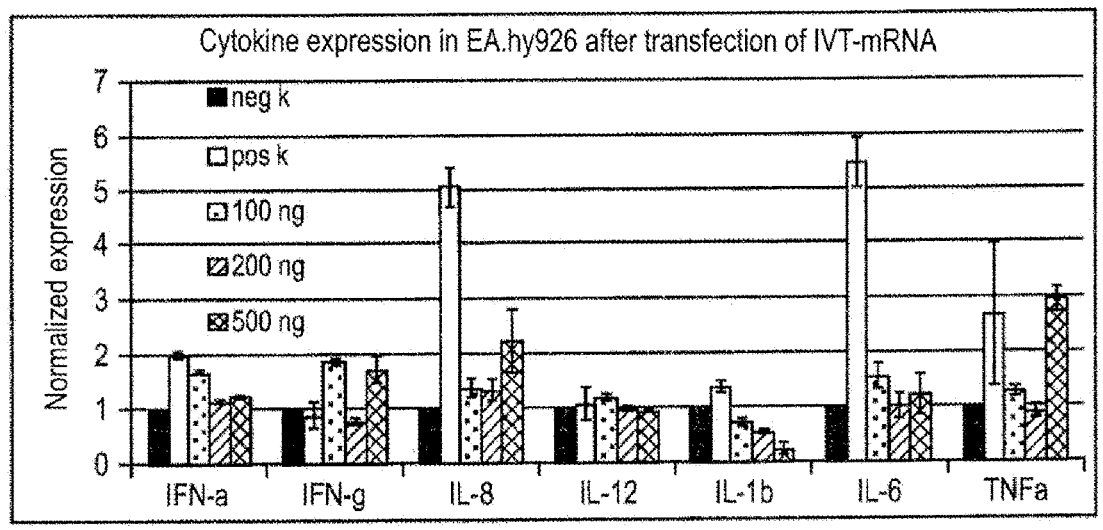
FIG. 8: Immune activation of EA.hy926 cells after the transfection of IVT-ELN-mRNA; the expressions were normalized to the housekeeping gene GAPDH. The negative controls were set to 1.

The following day, cells were lysed and the RNA was extracted with Aurum Total RNA Mini Kit (Biorad). The RNA-concentration was measured and 40 ng of each sample was used for cDNA-synthesis with iScript cDNA-synthesis kit (Biorad). The generated cDNA was used diluted in (qRT)-PCR reactions with the iQ SYBR Green Supermix (Biorad) in triplicates for each sample, combined with a specific primer pair for IFN-Ɐ, IFN-γ, IL-1 B, IL-12, IL-6, IL-8, TNF-α and a GAPDH-specific primer pair. For the quantification of the immune marker expression levels a qRT-PCR was performed in 96-well plates in the CFX Connect Real-Time PCR detection system (Biorad) (FIG. 8). The results show that the in vitro synthesized elastin-mRNA does only cause a very low activation of cytokines in this highly sensitive assay.

12. Coating of Coronary Stents with eGFP-mRNA

In another experiment the in vivo expression of eGFP via IVT-mRNA, coated on coronary stents was examined. The in vitro synthesis of the eGFP-mRNA was effected with the plasmid construct pcDNA3.3_eGFP as described in Warren et al. (l.c.). The plasmid was provided by the authors via Addgene (Cambridge, MA, USA).

BMS coronary stents 3×20 mm of Qualimed (Winsen, Germany) were dip-coated, in an emulsion of 70 μg in vitro transcribed eGFP-mRNA complexed with 20 μL of Lipofectamin2000 in nuclease free water and 150 μg of polyactic-co-glycolic acid RESOMER® RG 502 H (Sigma Aldrich) solved in ethyl acetate.

The study was performed in accordance with the German animal welfare law and the recommendations on the care and use of laboratory animals postulated by the FELASA (Federation of European Laboratoy Animal Science Associations). All protocols and procedures were approved by the Animal Care and Welfare Commission of the University of Tubingen.

For this study two female pigs of approx. 65 kg (German land race) supplied by a local "specific pathogen-free" (SPF) breeding facility were used for this study and included in the analysis. After arrival at the animal facility of the University of Tubingen, all animals were allowed one week of adaptation prior to the intervention. During this period clinical examinations were carried out to ensure the health status, especially in consideration of the cardiovascular system.

The stents were implanted via a balloon catheter (3 mm) into the left and right coronary arteries of each pig and expanded. The location of the stents was displayed with help of an X-ray apparatus (C-Bogen) and radiopaque material. An overstretching of the arteries was provoqued intentionally. After the implantation, the animals received heparin and clopidogrel to prevent postoperative thromboses.

44 hours after the implantation of the coated stents, the pigs were euthanized. The "stented" vessels were isolated and fixed overnight in 4% formaldehyde.

For the fluorescence analysis, the stents were embedded in methylmetacrylate based embedding system Technovit® 9100 from HeraeusKulzer (Wehrheim, Germany), and analyzed by fluorescence intensity decay shape analysis microscopy FIDSAM (fluorescence intensity decay shape analysis microscopy) at the Institute of Analytical Chemistry of the University of Tubingen.

Figure 9:
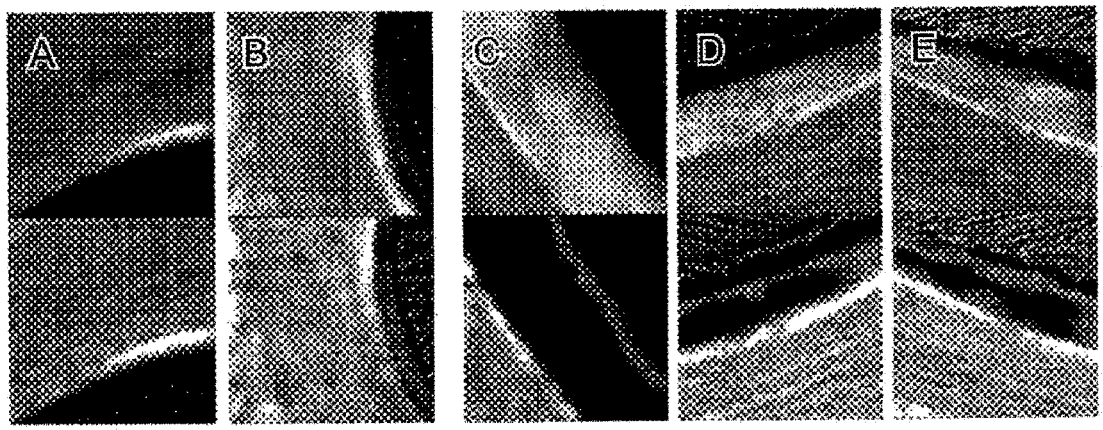
FIG. 9: Detection of the reporter gene expression: microscopic images of "stented" vessels, focus on the border between stent and tissue. A, B: negative controls (uncoated stents). C-E: eGPF-mRNA-coated stents. The size of the images corresponds to an area of 30×30 μm. Upper picture: original image. Lower picture: images with FIDSAM and contrast correction.

The result is shown in FIG. 9. There the part of fluorescent tissue visible after substraction of the autofluorescence is shown. This fluorescence is only due to the induced eGFP expression and therefore the evidence for efficient uptake and translation of the IVT-mRNA encoding eGFP by cells surrounding the stent material.

13. Pig Skin Model

Figure 10:
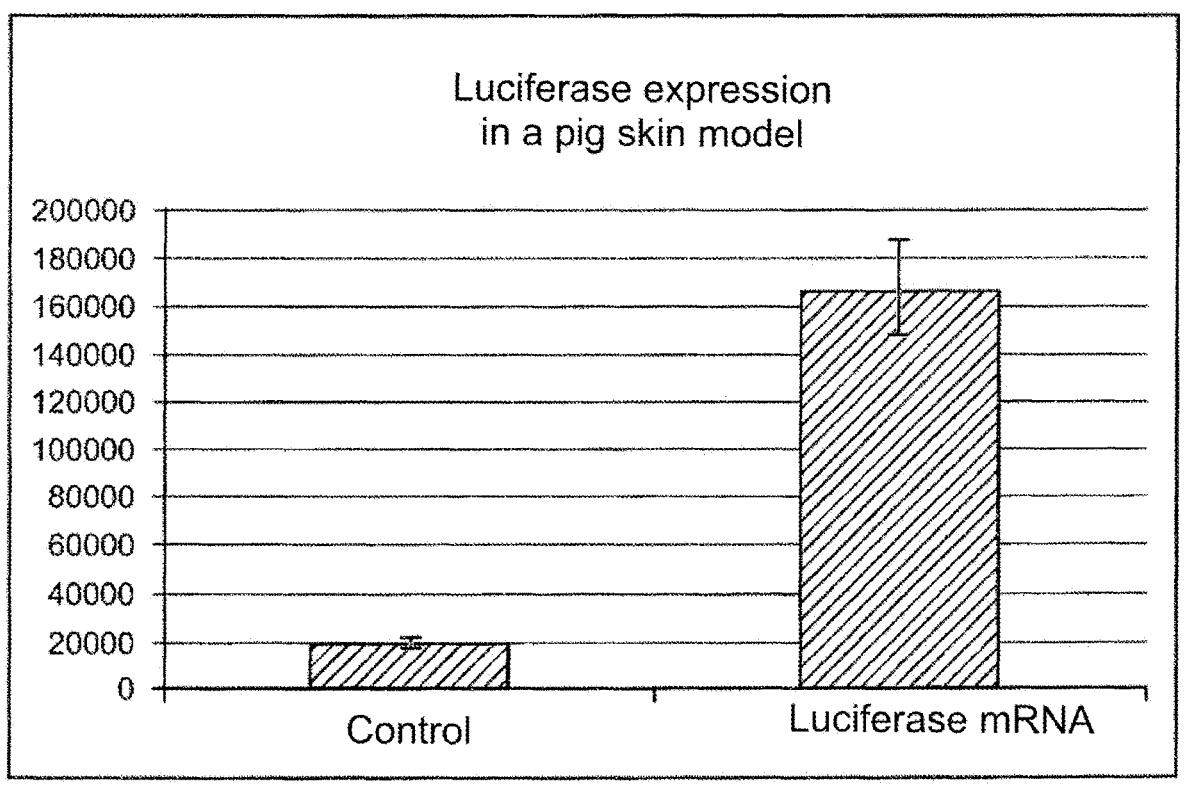
FIG. 10: Detection of the Luciferase expression in pig skin after transfection with Luciferase mRNA

A pig skin model was established to detect the synthesis of the mRNA-induced elastin in the skin. In the first experiments 2.5 μg of Luciferase mRNA/Lipofectamin 2000 complexes were injected into the skin. The skin was chopped after 24 h and for isolating the Luciferase the cells were lysed. The result is shown in FIG. 10. By means of the Luciferase Assay the successful transfection of the cells with Luciferase mRNA was demonstrated.

Sequences

SEQ ID No. 1: Nucleotide sequence of the IVT-elastin-mRNA (as used in the embodiments)

SEQ ID No. 2: Nucleotide sequence of the cDNA, derived from the mRNA of the human elastin, transcript variant 1 (NM_000501.2)

SEQ ID No. 3: Nucleotide sequence of the cDNA, derived from the mRNA of the human elastin, transcript variant 2 (NM_001081752.1)

SEQ ID No. 4: Nucleotide sequence of the cDNA, derived from the mRNA of the human elastin, transcript variant 3 (NM_001081753.1)

SEQ ID No. 5: Nucleotide sequence of the cDNA, derived from the mRNA of the human elastin, transcript variant 4 (NM_001081754.1)

SEQ ID No. 6: Nucleotide sequence of the cDNA, derived from the mRNA of the human elastin, transcript variant 5 (NM_001081755.1)

SEQ ID No. 7: Amino acid sequence of the elastin isoform a [*Homo sapiens*] (NP_00049.2)

SEQ ID No. 8: Amino acid sequence of the elastin isoform b [*Homo sapiens*] (NP_001075221.1)

SEQ ID No. 9: Amino acid sequence of the elastin isoform c [*Homo sapiens*] (NP_001075222.1)

SEQ ID No. 10: Amino acid sequence of the elastin isoform d [*Homo sapiens*] (NP_001075223.1)

SEQ ID No. 11: Amino acid sequence of the elastin isoform e [*Homo sapiens*] (NP_001075224.1)

What is claimed is:

1. A method for the induction of the synthesis of elastic fibrous protein in an organism, comprising the following steps:
   (1) providing a polyribonucleotide, and
   (2) administering said polyribonucleotide in or to cells of an organism to synthesize elastin/tropoelastin in said cells, wherein said polyribonucleotide encodes elastin/tropoelastin and comprises at least two polyribonucleotide stabilizing chemical modifications, wherein at least approximately 25% to 50% of the uridines of the polyribonucleotide are replaced by pseudouridines (Ψ) and at least approximately 25% to 50% of the cytidines of the polyribonucleotide are replaced by 5-methylcytidines (m5C) to stabilize the polyribonucleotide; and wherein level of synthesized elastin/tropoelastin in said cells is approximately sixfold to tenfold as compared to level of synthesized elastin/tropoelastin in cells to which unmodified polyribonucleotide encoding elastin/tropoelastin is administered.

2. The method of claim 1, wherein said polyribonucleotide is an mRNA.

3. The method of claim 1, wherein said polyribonucleotide further comprises a chemically modified uridine selected from the group consisting of: 5-methyluridine, 5-idouridine, 4-thiouridine, 5-bromouridine, 2'-methyl-2'-deoxyuridine, 2'-amino-2'-deoxyuridine, 2'-azido-2'-deoxyuridine, 2'-fluoro-2'-deoxyuridine, and combinations thereof.

4. The method of claim 1, wherein said polyribonucleotide further comprises a chemically modified cytidine selected from the group consisting of 5-methylcytidine, 3-methylcytidine, 2-thiocytidine, 2'-methyl-2'-deoxcytidin, 2'-amino-2'-deoxycytidine, 2'-fluoro-2'-deoxycytidine, 5-iodcytidine, 5-bromocytidine, and 2'-azido-2'-deoxycytidine, and combinations thereof.

5. The method of claim 4, wherein said polyribonucleotide further comprises a chemical modification selected from the group consisting of: a 5' cap structure, a poly (A) tail, a cap structure analog, and a strengthening of a translation-initiation sequence at the start codon AUG by the sequence (CCCCGC)aucGagAUG.

6. The method of claim 1, wherein said polyribonucleotide comprises the sequence of SEQ ID NO:1, wherein at least approximately 25% of the uridines of the polyribonucleotide are replaced by pseudouridines and at least approximately 25% of the cytidines of the polyribonucleotide are replaced by 5-methylcytidines.

7. The method of claim 1, wherein said polyribonucleotide encodes an amino acid sequence selected from the group consisting of: SEQ ID NO: 7, SEQ ID NO: 8, SEQ ID NO: 9, SEQ ID NO: 10, and SEQ ID NO: 11.

8. The method of claim 1, wherein said polyribonucleotide is configured for any of the following indications: the induction of the synthesis of elastin/tropoelastin, in age-related loss of elasticity of the skin (wrinkle formation), for promoting wound healing, and for the recovery of the elasticity of vaginal tissue, soft and hard tissue of the periodontium.

9. The method of claim 1, wherein said polyribonucleotide is configured for the treatment of a deficient synthesis of elastin/tropoelastin.

10. The method of claim 1, wherein said polyribonucleotide is configured for the treatment of a disease selected from the group consisting of: arteriosclerosis, aortic stenosis, aortic aneurysm, pulmonary emphysema, dermatochalasis, Williams-Beuren syndrome, and sub valvular innate aortic stenosis (SVAS).

11. The method of claim 1, wherein said polyribonucleotide is provided in a pharmaceutically acceptable formulation.

12. The method of claim 1, wherein said polyribonucleotide is provided in a cosmetically acceptable formulation.

13. The method of claim 1, wherein the level of synthesized elastin/tropoelastin in the cells is approximately tenfold as compared to level of synthesized elastin/tropoelastin in cells to which unmodified polyribonucleotide encoding elastin/tropoelastin is administered.

14. The method of claim 1, wherein in said polyribonucleotide approximately 25% of the uridines of the polyribonucleotide are replaced by pseudouridines (Ψ) and approximately 25% of the cytidines of the polyribonucleotide are replaced by 5-methylcytidines (m5C).

15. The method of claim 1, wherein in addition an immune-suppressive agent is administered in or to said organism.

16. The method of claim 1, wherein the polyribonucleotide encodes an amino acid sequence selected from the group consisting of: SEQ ID NO: 8, SEQ ID NO: 9, SEQ ID NO: 10, and SEQ ID NO: 11.

17. The method of claim 1, wherein the polyribonucleotide encodes an amino acid sequence selected from the group consisting of: SEQ ID NO: 9, SEQ ID NO: 10, and SEQ ID NO: 11, and which composition is configured to cause a lower level of IL-6 activation as compared to a level of IL-6 activation caused by a comparable amount of the immunostimulant polyinosinic/polycytidylic acid.

18. The method of claim 1, wherein said polyribonucleotide is provided as comprised by a medical patch or a vascular implant.

* * * * *

SEQUENCE LISTING

```
<160> NUMBER OF SEQ ID NOS: 11

<210> SEQ ID NO 1
<211> LENGTH: 3196
<212> TYPE: RNA
<213> ORGANISM: Artificial sequence
<220> FEATURE:
<223> OTHER INFORMATION: Synthetic construct

<400> SEQUENCE: 1
auggcgdguc ugacggcggc ggccccgcgg cccggagucc uccugcuccu gcuguccauc      60 cuccacccu cucggccugg aggggucccu ggggccauuc cugguggagu uccuggagga     120
gucuuuuauc caggggcugg ucucggagcc cuuggaggag gagcgcuggg gccuggaggc     180
aaaccucuua agccaguucc cggagggcuu gcgggugcug gccuuggggc agggcucggc     240
gccuuccccg caguuaccuu uccgggggcu cuggugccug guggaguggc ugacgcugcu     300
gcagccuaua aagcugcuaa ggcuggcgcu gggcuuggug gugucccagg aguugguggc     360
uuaggagugu cugcagguge gguggucucu cagccuggag ccggagugaa gccugggaaa     420 gugccggdgug ugggcugcc agguguauac ccagguggcg ugcucccagg agcucgguuc     480 cccgguguqg gggugcuccc uggaguuccc acuggagcag gaguuaagcc caaggcucca     540
```

```
gguguaggug gagcuuuugc uggaauccca ggaguuggac ccuuuggggg accgcaaccu     600 ggaguccac ugggguaucc caucaaggcc cccaagcugc cugguggcua uggacugccc      660
uacaccacag ggaaacugcc cuauggcuau ggcccggag  gaguggcugg ugcagcgggc     720
aaggcugguu acccaacagg gacaggggu ggccccagg   cagcagcagc agcggcagcu    780
aaagcagcag caaaguucgg ugcuggagca gccggagucc ucccggugu uggaggggcu      840 gguguuccug gcgugccugg ggcaauuccu ggaauggag  gcaucgcagg cguugggacu     900
ccagcugcag cugcagcugc agcagcagcc gcuaaggcag ccaaguaugg agcugcugca     960
ggcuuagugc cuggugggcc aggcuuuggc ccgggaguag uuggugucccaggagcuggc    1020 guuccaggug uuggugucccaggagcuggg auuccaguug ucccaggugc ugggaucccac   1080 ggugcugcgg uuccagggu ugugucacca gaagcagcug cuaaggcagc ugcaaaggca    1140
gccaaauacg gggccaggcc cggagucgga guuggaggca uccuacuua cggguugga     1200 gcuggggcu  uucccggcuu uggugucgga gucgaggua ucccuggagu cgcaggguc     1260 ccuggugucg gagguguucc cggagucgga gguguccgg gaguuggcau ucccccgaa     1320 gcucaggcag cagcugccgc caaggcugcc aaguacggag uggggacccc agcagcugca   1380
gcugcuaaag cagccgccaa agccgcccag uuuggguuag uuccuggugu cggcguggcu   1440
ccuggaguug gcguggcucc ugguucggu guggcuccug gaguuggcuu ggcuccugga    1500
guuggcgugg uccuggagu uggugugcu ccggcguug gcguggcucc cggcauuggc     1560 ccuggugag uugcagcugc agcaaaaucc gcugccaagg uggcugccaa agcccagcuc    1620
cgagcugcag cugggcuugg ugcuggcauc ccuggacuug gaguuggugu cggcguccca   1680
ggacuuggag uuggugcugg uguuccugga cuuggaguug gugcugggu uccuggcuuc    1740 ggggcaguac cuggagcccu ggcugccgcu aaagcagcca aauauggagc agcagugccu   1800 ggggucccuug gagggcucgg ggcucucggu ggaguaggca ucccaggcgg ugguggugga  1860
gccggacccg ccgccgccgc ugccgcagcc aaagcugcug ccaaagccgc ccaguuuggc   1920 cuaguggag ccgcugggcu cggaggacuc ggagucggag ggcuuggagu ccaggguguu   1980
gggggccuug gagguauacc uccagcugca gccgcuaaag cagcuaaaua cggugcugcu   2040
ggccuuggag uguccuagg ggugccggg caguucccac uuggaggagu ggcagcaaga     2100
ccuggcuucg gauugucucc cauuucccca ggugggccu gccugggaa gcuugugcc      2160 cggaagagaa aaugagcuuc cuaggacccc ugacucacga ccucaucaac guggugcua    2220 cugcuugug gaaugua  acccuuugua accccauccc augccccucc gacucccac       2280 cccaggaggg aacgggcagg ccgggcggcc uugcagaucc acagggcaag gaaacaagag   2340
gggagcggcc aagugcccg accaggaggc ccccuacuuc agaggcaagg ccauggugu     2400 ccuggccccc caccccauccc cuucccaccu aggagcuccc ccuccacaca gccuccaucu   2460
ccaggggaac uuggugcuac acgcuggugc ucuuaucuuc cggggggag  ggaggaggga   2520 aggugggccc cucggggaac ccccuaccug gggcucucu aaagauggug cagacacuuc    2580
cugggcaguc ccagcucccc cugcccacca ggaccaccg uuggcugcca uccaguuggu    2640
acccaagcac cugaagccuc aaagcuggau ucgcucuagc aucccuccuc uccggggucc   2700
acuuggccgu cuccucccca ccgaucgcug uucccacau cuggggcgcu uuugggguugg   2760 aaaaccaccc cacacuggga auagccaccu ugcccuugua gaauccauc cgcccaucgu    2820 ccauucaucc aucggcucgu ccauccaugu cccaguuga ccgcccggca ccacuagcug    2880
```

| | |
|---|---:|
| gcuggguḡca cccaccauca accugguuga ccugucaugg ccgccugugc ccugccucca | 2940 |
| ccccauccu acacucccc agggcgugcg gggcugugca gacuggggug ccaggcaucu | 3000 |
| ccucccacc cggggugucc ccacaugcag uacuguauac ccccauccc ucccucgguc | 3060 |
| cacugaacuu cagagcaguu cccauuccug ccccgcccau cuuuugugu cucgcuguga | 3120 |
| uagaucaaua aauauuuuau uuuuugucc ggaaaaaaaa aaaaaaaaa aaaaaaaaa | 3180 |
| aaaaaaaaaa aaaaa | 3196 |

<210> SEQ ID NO 2
<211> LENGTH: 3480
<212> TYPE: DNA
<213> ORGANISM: Artificial sequence
<220> FEATURE:
<223> OTHER INFORMATION: Synthetic construct

<400> SEQUENCE: 2

| | |
|---|---:|
| ctccctctt ccctcacagc cgacgaggca acaattaggc tttggggata aaacgaggtg | 60 |
| cggagagcgg gctgggcat ttctccccga gatggcgggt ctgacggcgg cggccccgcg | 120 |
| gcccggagtc ctcctgctcc tgctgtccat cctccacccc tctcggcctg gagggtccc | 180 |
| tggggccatt cctggtggag ttcctggagg agtctttat ccaggggctg gtctcggagc | 240 |
| ccttggagga ggagcgctgg ggcctggagg caaacctctt aagccagttc ccggagggct | 300 |
| tgcgggtgct ggccttgggg cagggctcgg cgccttcccc gcagttacct ttccggggc | 360 |
| tctggtgcct ggtggagtgg ctgacgctgc tgcagcctat aaagctgcta aggctggcgc | 420 |
| tgggcttggt ggtgtcccag gagttggtgg cttaggagtg tctgcaggtg cggtggttcc | 480 |
| tcagcctgga gccggagtga agcctgggaa agtgccgggt gtgggctgc caggtgtata | 540 |
| cccaggtggc gtgctcccag gagctcggtt ccccggtgtg ggggtgctcc ctggagttcc | 600 |
| cactggagca ggagttaagc ccaaggctcc aggtgtaggt ggagcttttg ctggaatccc | 660 |
| aggagttgga cccttggggg gaccgcaacc tggagtccca ctggggtatc ccatcaaggc | 720 |
| ccccaagctg cctggtggct atggactgcc ctacaccaca gggaaactgc cctatggcta | 780 |
| tgggcccgga ggagtggctg gtgcagcggg caaggctggt tacccaacag ggacaggggt | 840 |
| tggccccag gcagcagcag cagcggcagc taaagcagca gcaaagttcg gtgctggagc | 900 |
| agccggagtc ctccctggtg ttggagggc tggtgttcct ggcgtgcctg ggcaattcc | 960 |
| tggaattgga ggcatcgcag gcgttgggac tccagctgca gctgcagctg cagcagcagc | 1020 |
| cgctaaggca gccaagtatg gagctgctgc aggcttagtg cctggtgggc caggctttgg | 1080 |
| cccgggagta gttggtgtcc caggagctgg cgttccaggt gttggtgtcc caggagctgg | 1140 |
| gattccagtt gtcccaggtg ctgggatccc aggtgctgcg gttccagggg ttgtgtcacc | 1200 |
| agaagcagct gctaaggcag ctgcaaaggc agccaaatac ggggccaggc ccggagtcgg | 1260 |
| agttggaggc attcctactt acggggttgg agctgggggc tttcccggct ttggtgtcgg | 1320 |
| agtcggaggt atccctggag tcgcaggtgt ccctggtgtc ggaggtgttc ccggagtcgg | 1380 |
| aggtgtcccg ggagttggca tttcccccga agctcaggca gcagctgccg ccaaggctgc | 1440 |
| caagtacgga gtgggaccc cagcagctgc agctgctaaa gcagccgcca agccgcccca | 1500 |
| gtttgggtta gttcctggtg tcggcgtggc tcctggagtt ggcgtggctc ctggtgtcgg | 1560 |
| tgtggctcct ggagttggct tggctcctgg agttggcgtg gctcctggag ttggtgtggc | 1620 |
| tcctggcgtt ggcgtggctc ccggcattgg ccctggtgga gttgcagctg cagcaaaatc | 1680 |
| cgctgccaag gtggctgcca agcccagct ccgagctgca gctgggcttg gtgctggcat | 1740 |

```
ccctggactt ggagttggtg tcggcgtccc tggacttgga gttggtgctg gtgttcctgg    1800
acttggagtt ggtgctggtg ttcctggctt cggggcagta cctggagccc tggctgccgc    1860
taaagcagcc aaatatggag cagcagtgcc tggggtcctt ggagggctcg gggctctcgg    1920
tggagtaggc atcccaggcg gtgtggtggg agccggaccc gccgccgccg ctgccgcagc    1980
caaagctgct gccaaagccg cccagtttgg cctagtggga gccgctgggc tcggaggact    2040
cggagtcgga gggcttggag ttccaggtgt tgggggcctt ggaggtatac ctccagctgc    2100
agccgctaaa gcagctaaat acggtgctgc tggccttgga ggtgtcctag ggggtgccgg    2160
gcagttccca cttggaggag tggcagcaag acctggcttc ggattgtctc ccattttccc    2220
aggtggggcc tgcctgggga aagcttgtgg ccggaagaga aaatgagctt cctaggaccc    2280
ctgactcacg acctcatcaa cgttggtgct actgcttggt ggagaatgta aaccctttgt    2340
aaccccatcc catgcccctc cgactcccca ccccaggagg aacgggcag gccgggcggc    2400 cttgcagatc cacagggcaa ggaaacaaga ggggagcggc caagtgcccc gaccaggagg    2460 cccccctactt cagaggcaag ggccatgtgg tcctggcccc ccaccccatc ccttcccacc    2520
taggagctcc ccctccacac agcctccatc tccaggggaa cttggtgcta cacgctggtg    2580
ctcttatctt cctgggggga ggaggaggg aagggtggcc cctcggggaa cccccctacct    2640 ggggctcctc taaagatggt gcagacactt cctgggcagt cccagctccc cctgcccacc    2700
aggacccacc gttggctgcc atccagttgg tacccaagca cctgaagcct caaagctgga    2760
ttcgctctag catccctcct ctcctgggtc cacttggccg tctcctcccc accgatcgct    2820
gttccccaca tctgggcgc ttttgggttg gaaaaccacc ccacactggg aatagccacc    2880
ttgcccttgt agaatccatc cgcccatccg tccattcatc catcggtccg tccatccatg    2940
tccccagttg accgccggc accactagct ggctgggtgc acccaccatc aacctggttg    3000
acctgtcatg gccgcctgtg ccctgcctcc accccatcc tacactcccc cagggcgtgc    3060
ggggctgtgc agactgggt gccaggcatc tcctccccac ccggggtgtc cccacatgca    3120
gtactgtata ccccccatcc ctccctcggt ccactgaact tcagagcagt tcccattcct    3180
gccccgccca tcttttgtg tctcgctgtg atagatcaat aaatatttta ttttttgtcc    3240
tggatatttg gggattattt ttgattgttg atattctctt ttggttttat tgttgtggtt    3300
cattgaaaaa aaaagataat tttttttttct gatccgggga gctgtatccc cagtagaaaa    3360
aacattttaa tcactctaat ataactctgg atgaaacaca ccttttttttt taataagaaa    3420 agagaattaa ctgcttcaga aatgactaat aaatgaaaaa cctttaaagg aaaaaaaaaa    3480
```

<210> SEQ ID NO 3
<211> LENGTH: 3339
<212> TYPE: DNA
<213> ORGANISM: Artificial sequence
<220> FEATURE:
<223> OTHER INFORMATION: Synthetic construct

<400> SEQUENCE: 3

```
ctccctcttt ccctcacagc cgacgaggca acaattaggc tttggggata aaacgaggtg      60
cggagagcgg gctgggcat ttctccccga gatggcgggt ctgacggcgg cggccccgcg     120
gcccggagtc ctcctgctcc tgctgtccat cctccacccc tctcggcctg aggggtccc     180 tggggccatt cctggtggag ttcctggagg agtcttttat ccagcgctgg ggcctggagg     240
caaacctctt aagccagttc ccggagggct tgcgggtgct ggccttgggg cagggctcgg     300
```

```
cgccttcccc gcagttacct ttccgggggc tctggtgcct ggtggagtgg ctgacgctgc    360
tgcagcctat aaagctgcta aggctggcgc tgggcttggt ggtgtcccag gagttggtgg    420
cttaggagtg tctgcaggtg cggtggttcc tcagcctgga gccggagtga agcctgggaa    480
agtgccgggt gtggggctgc caggtgtata cccaggtggc gtgctcccag gagctcggtt    540
ccccggtgtg ggggtgctcc ctggagttcc cactggagca ggagttaagc ccaaggctcc    600
aggtgtaggt ggagcttttg ctggaatccc aggagttgga ccctttgggg gaccgcaacc    660
tggagtccca ctggggtatc ccatcaaggc ccccaagctg cctggtggct atggactgcc    720
ctacaccaca gggaaactgc cctatggcta tgggcccgga ggagtggctg gtgcagcggg    780
caaggctggt tacccaacag ggacaggggt tggcccccag gcagcagcag cagcggcagc    840
taaagcagca gcaaagttcg gtgctggagc agcggagtc ctccctggtg ttggaggggc    900
tggtgttcct ggcgtgcctg gggcaattcc tggaattgga ggcatcgcag gcgttgggac    960
tccagctgca gctgcagctg cagcagcagc cgctaaggca gccaagtatg gagctgctgc   1020
aggcttagtg cctggtgggc caggcttggg cccgggagta gttggtgtcc caggagctgg   1080
cgttccaggt gttggtgtcc caggagctgg gattccagtt gtcccaggtg ctgggatccc   1140
aggtgctgcg gttccagggg ttgtgtcacc agaagcagct gctaaggcag ctgcaaaggc   1200
agccaaatac ggggccaggc ccggagtcgg agttggaggc attcctactt acggggttgg   1260
agctgggggc tttcccggct ttggtgtcgg agtcggagga tccctggag tcgcaggtgt   1320 ccctggtgtc ggaggtgttc ccggagtcgg aggtgtcccg ggagttggca tttcccccga   1380
agctcaggca gcagctgccg ccaaggctgc caagtacggg ttagttcctg gtgtcggcgt   1440
ggctcctgga gttggcgtgg ctcctggtgt cggtgtggct cctggagttg gcttggctcc   1500
tggagttggc gtggctcctg gagttggtgt ggctcctggc gttggcgtgg ctcccggcat   1560
tggccctggt ggagttgcag ctgcagcaaa atccgctgcc aaggtggctg ccaaagccca   1620
gctccgagct gcagctgggc ttggtgctgg catccctgga cttggagttg gtgtcggcgt   1680
ccctggactt ggagttggtg ctggtgttcc tggacttgga gttggtgctg gtgttcctgg   1740
cttcggggca gtacctggag ccctggctgc cgctaaagca gccaaatatg gagcagcagt   1800
gcctggggtc cttggagggc tcggggctct cggtggagta ggcatcccag gcggtgtggt   1860
gggagccgga cccgccgccg ccgctgccgc agccaaagct gctgccaaag ccgcccagtt   1920
tggcctagtg ggagccgctg ggctcggagg actcggagtc ggagggcttg gagttccagg   1980
tgttgggggc cttggaggta tacctccagc tgcagccgct aaagcagcta aatacggagt   2040
ggcagcaaga cctggcttcg gattgtctcc cattttccca ggtggggcct gcctggggaa   2100
agcttgtggc cggaagagaa aatgagcttc ctaggacccc tgactcacga cctcatcaac   2160
gttggtgcta ctgcttggtg gagaatgtaa accctttgta accccatccc atgcccctcc   2220
gactccccac cccaggaggg aacgggcagg ccgggcggcc ttgcagatcc acagggcaag   2280
gaaacaagag gggagcggcc aagtgccccg accaggaggc cccctacttc agaggcaagg   2340
gccatgtggt cctggccccc caccccatcc cttcccacct aggagctccc cctccacaca   2400
gcctccatct ccaggggaac ttggtgctac acgctggtgc tcttatcttc tgggggag    2460 ggaggaggga agggtggccc ctcggggaac cccctacctg gggctcctct aaagatggtg    2520
cagacacttc ctgggcagtc ccagctcccc ctgcccacca ggacccaccg ttggctgcca    2580
tccagttggt acccaagcac ctgaagcctc aaagctggat tcgctctagc atccctcctc    2640
tcctgggtcc acttggccgt ctcctcccca ccgatcgctg ttccccacat ctggggcgct    2700
```

| | |
|---|---|
| tttgggttgg aaaaccaccc cacactggga atagccacct tgcccttgta gaatccatcc | 2760 |
| gcccatccgt ccattcatcc atcggtccgt ccatccatgt ccccagttga ccgcccggca | 2820 |
| ccactagctg gctgggtgca ccaccatca acctggttga cctgtcatgg ccgcctgtgc | 2880 |
| cctgcctcca cccccatcct acactccccc agggcgtgcg gggctgtgca gactggggtg | 2940 |
| ccaggcatct cctccccacc cggggtgtcc ccacatgcag tactgtatac ccccatccc | 3000 |
| tccctcggtc cactgaactt cagagcagtt cccattcctg cccgcccat ctttttgtgt | 3060 |
| ctcgctgtga tagatcaata aatattttat tttttgtcct ggatatttgg ggattatttt | 3120 |
| tgattgttga tattctcttt tggttttatt gttgtggttc attgaaaaaa aaagataatt | 3180 |
| ttttttctg atccggggag ctgtatcccc agtagaaaaa acatttaat cactctaata | 3240 |
| taactctgga tgaaacacac cttttttttt aataagaaaa gagaattaac tgcttcagaa | 3300 |
| atgactaata aatgaaaaac ctttaaagga aaaaaaaa | 3339 |

<210> SEQ ID NO 4
<211> LENGTH: 3384
<212> TYPE: DNA
<213> ORGANISM: Artificial sequence
<220> FEATURE:
<223> OTHER INFORMATION: Synthetic construct

<400> SEQUENCE: 4

| | |
|---|---|
| ctccctctttt ccctcacagc cgacgaggca acaattaggc tttggggata aaacgaggtg | 60 |
| cggagagcgg gctggggcat ttctccccga gatggcgggt ctgacggcgg cggccccgcg | 120 |
| gcccggagtc ctcctgctcc tgctgtccat cctccacccc tctcggcctg gagggggtccc | 180 |
| tggggccatt cctggtggag ttcctggagg agtcttttat ccaggggctg gtctcggagc | 240 |
| ccttggagga ggagcgctgg ggcctggagg caaacctctt aagccagttc ccggagggct | 300 |
| tgcgggtgct ggccttgggg cagggctcgg cgccttcccc gcagttacct ttccgggggc | 360 |
| tctggtgcct ggtggagtgg ctgacgctgc tgcagcctat aaagctgcta aggctggcgc | 420 |
| tgggcttggt ggtgtcccag gagttggtgg cttaggagtg tctgcagccc cttctgtgcc | 480 |
| aggtgcggtg gttcctcagc ctggagccgg agtgaagcct gggaaagtgc cgggtgtggg | 540 |
| gctgccaggt gtatacccag gtggcgtgct cccaggagct cggttccccg gtgtggggt | 600 |
| gctccctgga gttcccactg gagcaggagt taagcccaag gctccaggtg taggtggagc | 660 |
| ttttgctgga atcccaggag ttggaccctt tgggggaccg caacctggag tcccactggg | 720 |
| gtatcccatc aaggcccca agctgcctgg tggctatgga ctgccctaca ccacagggaa | 780 |
| actgccctat ggctatgggc ccggaggagt ggctggtgca gcgggcaagg ctggttaccc | 840 |
| aacagggaca ggggttggcc cccaggcagc agcagcagcg gcagctaaag cagcagcaaa | 900 |
| gttcggtgct ggagcagccg gagtcctccc tggtgttgga ggggctggtg ttcctggcgt | 960 |
| gcctggggca attcctggaa ttggaggcat cgcaggcgtt gggactccag ctgcagctgc | 1020 |
| agctgcagca gcagccgcta aggcagccaa gtatggagct gctgcaggct tagtgcctgg | 1080 |
| tgggccaggc tttggcccgg gagtagttgg tgtcccagga gctggcgttc caggtgttgg | 1140 |
| tgtcccagga gctgggattc cagttgtccc aggtgctggg atcccaggtg ctgcggttcc | 1200 |
| aggggttgtg tcaccagaag cagctgctaa ggcagctgca aaggcagcca atacggggc | 1260 |
| caggcccgga gtcggagttg gaggcattcc tacttacggg gttggagctg ggggctttcc | 1320 |
| cggctttggt gtcggagtcg gaggtatccc tggagtcgca ggtgtccctg gtgtcggagg | 1380 |

```
tgttcccgga gtcggaggtg tcccgggagt tggcatttcc ccgaagctc  aggcagcagc    1440 tgccgccaag gctgccaagt acgggttagt tcctggtgtc ggcgtggctc ctggagttgg    1500
cgtggctcct ggtgtcggtg tggctcctgg agttggcttg gctcctggag ttggcgtggc    1560
tcctggagtt ggtgtggctc ctggcgttgg cgtggctccc ggcattggcc ctggtggagt    1620
tgcagctgca gcaaaatccg ctgccaaggt ggctgccaaa gcccagctcc gagctgcagc    1680
tgggcttggt gctggcatcc ctggacttgg agttggtgtc ggcgtccctg gacttggagt    1740
tggtgctggt gttcctggac ttggagttgg tgctggtgtt cctggcttcg gggcagtacc    1800
tggagccctg gctgccgcta aagcagccaa atatggagca gcagtgcctg gggtccttgg    1860
agggctcggg gctctcggtg gagtaggcat cccaggcggt gtggtgggag ccggacccgc    1920
cgccgccgct gccgcagcca aagctgctgc caaagccgcc cagtttggcc tagtgggagc    1980
cgctgggctc ggaggactcg gagtcggagg gcttggagtt ccaggtgttg ggggccttgg    2040
aggtatacct ccagctgcag ccgctaaagc agctaaatac ggagtggcag caagacctgg    2100
cttcggattg tctcccattt tcccaggtgg ggcctgcctg gggaaagctt gtggccggaa    2160
gagaaaatga gcttcctagg acccctgact cacgacctca tcaacgttgg tgctactgct    2220
tggtggagaa tgtaaaccct ttgtaacccc atcccatgcc cctccgactc cccacccag    2280 gagggaacgg gcaggccggg cggccttgca gatccacagg gcaaggaaac aagaggggag    2340
cggccaagtg ccccgaccag gaggccccct acttcagagg caagggccat gtggtcctgg    2400 cccccaccc  catcccttcc cacctaggag ctcccctcc  acacagcctc catctccagg    2460
ggaacttggt gctacacgct ggtgctctta tcttcctggg gggagggagg agggaagggt    2520 ggccctcgg  ggaacccct  acctggggct cctctaaaga tggtgcagac acttcctggg    2580
cagtcccagc tccccctgcc caccaggacc caccgttggc tgccatccag ttggtaccca    2640
agcacctgaa gcctcaaagc tggattcgct ctagcatccc tcctctcctg ggtccacttg    2700
gccgtctcct ccccaccgat cgctgttccc cacatctggg gcgcttttgg gttggaaaac    2760
caccccacac tgggaatagc caccttgccc ttgtagaatc catccgccca tccgtccatt    2820
catccatcgg tccgtccatc catgtcccca gttgaccgcc cggcaccact agctggctgg    2880
gtgcacccac catcaacctg gttgacctgt catggccgcc tgtgccctgc ctccaccccc    2940
atcctacact ccccccaggc gtgcggggct gtgcagactg gggtgccagg catctcctcc    3000
ccacccgggg tgtccccaca tgcagtactg tataccccc  atccctccct cggtccactg    3060
aacttcagag cagttcccat tcctgccccg cccatctttt tgtgtctcgc tgtgatagat    3120
caataaatat tttatttttt gtcctggata tttgggggatt attttttgatt gttgatattc    3180 tcttttggtt ttattgttgt ggttcattga aaaaaaaga taattttttt ttctgatccg    3240
gggagctgta tccccagtag aaaaaacatt ttaatcactc taatataact ctggatgaaa    3300
cacacctttt tttttaataa gaaaagagaa ttaactgctt cagaaatgac taataaatga    3360 aaaacctta  aaggaaaaaaa aaaa                                         3384
```

<210> SEQ ID NO 5
<211> LENGTH: 3441
<212> TYPE: DNA
<213> ORGANISM: Artificial sequence
<220> FEATURE:
<223> OTHER INFORMATION: Synthetic construct

<400> SEQUENCE: 5

```
ctccctcttt ccctcacagc cgacgaggca acaattaggc tttggggata aaacgaggtg      60
```

```
cggagagcgg gctggggcat ttctccccga gatggcgggt ctgacggcgg cggccccgcg    120
gcccggagtc ctcctgctcc tgctgtccat cctccacccc tctcggcctg gaggggtccc    180
tggggccatt cctggtggag ttcctggagg agtcttttat ccaggggctg gtctcggagc    240
ccttggagga ggagcgctgg ggcctggagg caaacctctt aagccagttc ccggagggct    300
tgcgggtgct ggccttgggg cagggctcgg cgccttcccc gcagttacct ttccggggc     360 tctggtgcct ggtggagtgg ctgacgctgc tgcagcctat aaagctgcta aggctggcgc    420
tgggcttggt ggtgtcccag gagttggtgg cttaggagtg tctgcagccc cttctgtgcc    480
aggtgcggtg gttcctcagc ctggagccgg agtgaagcct gggaaagtgc cgggtgtggg    540
gctgccaggt gtatacccag gtggcgtgct cccaggagct cggttccccg gtgtggggt    600 gctccctgga gttcccactg gagcaggagt taagcccaag gctccaggtg taggtggagc    660
ttttgctgga atcccaggag ttggacccctt tgggggaccg caacctggag tcccactggg   720
gtatcccatc aaggcccca agctgcctgg tggctatgga ctgccctaca ccacagggaa     780
actgccctat ggctatgggc ccggaggagt ggctggtgca gcgggcaagg ctggttaccc    840
aacagggaca ggggttggcc cccaggcagc agcagcagcg gcagctaaag cagcagcaaa    900
gttcggtgct ggagcagccg gagtcctccc tggtgttgga ggggctggtg ttcctggcgt    960
gcctggggca attcctggaa ttggaggcat cgcaggcgtt gggactccag ctgcagctgc   1020
agctgcagca gcagccgcta aggcagccaa gtatggagct gctgcaggct tagtgcctgg   1080
tgggccaggc tttggcccgg gagtagttgg tgtcccagga gctggcgttc caggtgttgg   1140
tgtcccagga gctgggattc cagttgtccc aggtgctggg atcccaggtg ctgcggttcc   1200
agggggtgtg tcaccagaag cagctgctaa ggcagctgca aaggcagcca aatacggggc   1260
caggcccgga gtcggagttg gaggcattcc tacttacggg gttggagctg ggggctttcc   1320
cggctttggt gtcggagtcg gaggtatccc tggagtcgca ggtgtccctg gtgtcggagg   1380
tgttcccgga gtcggaggtg tcccgggagt tggcatttcc cccgaagctc aggcagcagc   1440
tgccgccaag gctgccaagt acggagtggg gaccccagca gctgcagctg ctaaagcagc   1500
cgccaaagcc gcccagtttg ggttagttcc tggtgtcggc gtggctcctg gagttggcgt   1560
ggctcctggt gtcggtgtgg ctcctggagt tggcttggct cctggagttg gcgtggctcc   1620
tggagttggt gtggctcctg gcgttggcgt ggctcccggc attggccctg gtggagttgc   1680
agctgcagca aaatccgctg ccaaggtggc tgccaaagcc cagctccgag ctgcagctgg   1740
gcttggtgct ggcatccctg gacttggagt tggtgtcggc gtccctggac ttggagttgg   1800
tgctggtgtt cctggacttg gagttggtgc tggtgttcct ggcttcgggg cagtacctgg   1860
agccctggct gccgctaaag cagccaaata tggagcagca gtgcctgggg tccttggagg   1920
gctcggggct ctcggtggag taggcatccc aggcggtgtg gtgggagccg acccgccgc    1980 cgccgctgcc gcagccaaag ctgctgccaa agccgcccag tttggcctag tgggagccgc   2040
tgggctcgga ggactcggag tcggagggct tggagttcca ggtgttgggg ccttggagg    2100 tatacctcca gctgcagccg ctaaagcagc taaatacgga gtggcagcaa gacctggctt   2160
cggattgtct cccattttcc caggtggggc ctgcctgggg aaagcttgtg gccggaagag    2220
aaaatgagct tcctaggacc cctgactcac gacctcatca acgttggtgc tactgcttgg   2280
tggagaatgt aaacccttg taacccccatc ccatgcccct ccgactcccc accccaggag    2340
ggaacgggca ggccgggcgg ccttgcagat ccacagggca aggaaacaag agggagcgg    2400
```

| | |
|---|---|
| ccaagtgccc cgaccaggag gcccctact tcagaggcaa gggccatgtg gtcctggccc | 2460 |
| cccacccat cccttcccac ctaggagctc cccctccaca cagcctccat ctccagggga | 2520 |
| acttggtgct acacgctggt gctcttatct tcctgggggg agggaggagg aagggtggc | 2580 |
| ccctcgggga acccctacc tggggctcct ctaaagatgg tgcagacact tcctgggcag | 2640 |
| tcccagctcc ccctgcccac caggacccac cgttggctgc catccagttg gtacccaagc | 2700 |
| acctgaagcc tcaaagctgg attcgctcta gcatccctcc tctcctgggt ccacttggcc | 2760 |
| gtctcctccc caccgatcgc tgttccccac atctggggcg cttttgggtt ggaaaaccac | 2820 |
| cccacactgg gaatagccac cttgcccttg tagaatccat ccgccatcc gtccattcat | 2880 |
| ccatcggtcc gtccatccat gtccccagtt gaccgcccgg caccactagc tggctgggtg | 2940 |
| cacccaccat caacctggtt gacctgtcat ggccgcctgt gccctgcctc cacccccatc | 3000 |
| ctacactccc ccagggcgtg cggggctgtg cagactgggg tgccaggcat ctcctcccca | 3060 |
| cccggggtgt cccacatgc agtactgtat accccccatc cctccctcgg tccactgaac | 3120 |
| ttcagagcag ttcccattcc tgcccgccc atcttttgt gtctcgctgt gatagatcaa | 3180 |
| taaatattt attttttgtc ctggatattt ggggattatt tttgattgtt gatattctct | 3240 |
| tttggttta ttgttgtggt tcattgaaaa aaaaagataa ttttttttc tgatccgggg | 3300 |
| agctgtatcc ccagtagaaa aaacatttta atcactctaa tataactctg gatgaaacac | 3360 |
| acctttttt ttaataagaa aagagaatta actgcttcag aaatgactaa taatgaaaa | 3420 |
| acctttaaag gaaaaaaaaa a | 3441 |

<210> SEQ ID NO 6
<211> LENGTH: 3423
<212> TYPE: DNA
<213> ORGANISM: Artificial sequence
<220> FEATURE:
<223> OTHER INFORMATION: Synthetic construct

<400> SEQUENCE: 6

| | |
|---|---|
| ctccctcttt ccctcacagc cgacgaggca acaattaggc tttggggata aaacgaggtg | 60 |
| cggagagcgg gctggggcat ttctccccga gatggcgggt ctgacggcgg cggccccgcg | 120 |
| gcccggagtc ctcctgctcc tgctgtccat cctccacccc tctcggcctg gagggtccc | 180 |
| tggggccatt cctggtggag ttcctggagg agtcttttat ccaggggctg gtctcggagc | 240 |
| ccttggagga ggagcgctgg ggcctggagg caaacctctt aagccagttc ccggagggct | 300 |
| tgcgggtgct ggccttgggg cagggctcgg cgccttcccc gcagttacct ttccgggggc | 360 |
| tctggtgcct ggtggagtgg ctgacgctgc tgcagcctat aaagctgcta aggctggcgc | 420 |
| tgggcttggt ggtgtcccag gagttggtgg cttaggagtg tctgcaggtg cggtggttcc | 480 |
| tcagcctgga gccggagtga agcctgggaa agtgccgggt gtgggctgc aggtgtata | 540 |
| cccaggtggc gtgctcccag gagctcggtt cccggtgtg ggggtgctcc ctggagttcc | 600 |
| cactggagca ggagttaagc ccaaggctcc aggtgtaggt ggagcttttg ctggaatccc | 660 |
| aggagttgga cccttttggg gaccgcaacc tggagtccca ctggggtatc ccatcaaggc | 720 |
| ccccaagctg cctggtggct atggactgcc ctacaccaca gggaaactgc cctatggcta | 780 |
| tgggcccgga ggagtggctg gtgcagcggg caaggctggt tacccaacag ggacagggt | 840 |
| tggccccag gcagcagcag cagcggcagc taaagcagca gcaaagtcg gtgctggagc | 900 |
| agccggagtc ctccctggtg ttggaggggc tggtgttcct ggcgtgcctg ggcaattcc | 960 |
| tggaattgga ggcatcgcag gcgttgggac tccagctgca gctgcagctg cagcagcagc | 1020 |

```
cgctaaggca gccaagtatg gagctgctgc aggcttagtg cctggtgggc caggctttgg      1080
cccgggagta gttggtgtcc caggagctgg cgttccaggt gttggtgtcc caggagctgg      1140
gattccagtt gtcccaggtg ctgggatccc aggtgctgcg gttccagggg ttgtgtcacc      1200
agaagcagct gctaaggcag ctgcaaaggc agccaaatac ggggccaggc ccggagtcgg      1260
agttggaggc attcctactt acggggttgg agctgggggc tttcccggct tggtgtcgg      1320 agtcggaggt atccctggag tcgcaggtgt ccctggtgtc ggaggtgttc ccggagtcgg      1380
aggtgtcccg ggagttggca ttttcccccga agctcaggca gcagctgccg ccaaggctgc      1440
caagtacggg ttagttcctg gtgtcggcgt ggctcctgga gttggcgtgg ctcctggtgt      1500
cggtgtggct cctggagttg gcttggctcc tggagttggc gtggctcctg gagttggtgt      1560
ggctcctggc gttggcgtgg ctcccggcat tggccctggt ggagttgcag ctgcagcaaa      1620
atccgctgcc aaggtggctg ccaaagccca gctccgagct gcagctgggc ttggtgctgg      1680
catccctgga cttggagttg gtgtcggcgt ccctggactt ggagttggtg ctggtgttcc      1740
tggacttgga gttggtgctg gtgttcctgg cttcggggca gtacctggag ccctggctgc      1800
cgctaaagca gccaaaatg gagcagcagt gcctggggtc cttggagggc tcggggctct      1860
cggtggagta ggcatcccag gcggtgtggt gggagccgga cccgccgccg ccgctgccgc      1920
agccaaagct gctgccaaag ccgcccagtt tggcctagtg ggagccgctg ggctcggagg      1980
actcggagtc ggagggcttg gagttccagg tgttgggggc cttggaggta tacctccagc      2040
tgcagccgct aaagcagcta atacggtgc tgctggcctt ggaggtgtcc taggggtgc      2100 cgggcagttc ccacttggag gagtggcagc aagacctggc ttcggattgt ctcccatttt      2160
cccaggtggg gcctgcctgg ggaaagcttg tggccggaag agaaaatgag cttcctagga      2220
cccctgactc acgacctcat caacgttggt gctactgctt ggtggagaat gtaaacccctt      2280 tgtaaccccca tcccatgccc ctccgactcc ccaccccagg agggaacggg caggccgggc      2340
ggccttgcag atccacaggg caaggaaaca agagggaggc ggccaagtgc cccgaccagg      2400
aggcccccta cttcagaggc aagggccatg tggtcctggc ccccaccccc atcccttccc      2460
acctaggagc tcccctccca acacagcctc catctccaggg gaacttggtg ctacacgctg      2520
gtgctcttat cttcctgggg ggagggagga gggaagggtg gccccctcggg gaacccccta      2580 cctggggctc ctctaaagat ggtgcagaca cttcctgggc agtcccagct cccccctgccc      2640 accaggaccc accgttggct gccatccagt tggtacccaa gcacctgaag cctcaaaagct      2700 ggattcgctc tagcatccct cctctcctgg gtccacttgg ccgtctcctc ccaccgatc      2760 gctgttcccc acatctgggg cgcttttggg ttggaaaacc accccacact gggaatagcc      2820
accttgccct tgtagaatcc atccgcccat ccgtccattc atccatcggt ccgtccatcc      2880
atgtccccag ttgaccgccc ggcaccacta gctggctggg tgcacccacc atcaacctgg      2940
ttgacctgtc atggccgcct gtgccctgcc tccaccccca tcctacactc ccccagggcg      3000
tgcggggctg tgcagactgg ggtgccaggc atctcctccc cacccggggt gtccccacat      3060
gcagtactgt ataccccca tccctccctc ggtccactga acttcagagc agttcccatt      3120
cctgccccgc ccatcttttt gtgtctcgct gtgatagatc aataaatatt ttatttttg      3180 tcctggatat ttggggatta ttttgattg ttgatattct cttttggttt tattgttgtg      3240
gttcattgaa aaaaaagat aattttttt tctgatccgg ggagctgtat ccccagtaga      3300
aaaaacattt taatcactct aatataactc tggatgaaac acacctttttt ttttaataag      3360
```

```
aaaagagaat taactgcttc agaaatgact aataaatgaa aaacctttaa aggaaaaaaa    3420
aaa                                                                 3423
```

<210> SEQ ID NO 7
<211> LENGTH: 724
<212> TYPE: PRT
<213> ORGANISM: Homo sapiens
<220> FEATURE:
<221> NAME/KEY: MISC_FEATURE
<222> LOCATION: (1)..(724)
<223> OTHER INFORMATION: Elastin isoform a

<400> SEQUENCE: 7

```
Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
        115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Val Pro Gly Val Pro Gly Ala
        275                 280                 285

Ile Pro Gly Ile Gly Gly Ile Ala Gly Val Gly Thr Pro Ala Ala Ala
    290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335
```

```
Pro Gly Ala Gly Val Pro Gly Val Gly Val Pro Gly Ala Gly Ile Pro
                340                 345                 350

Val Val Pro Gly Ala Gly Ile Pro Gly Ala Ala Val Pro Gly Val Val
            355                 360                 365

Ser Pro Glu Ala Ala Ala Lys Ala Ala Ala Lys Ala Ala Lys Tyr Gly
        370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Val Pro Gly Val Gly Gly Val
            420                 425                 430

Pro Gly Val Gly Ile Ser Pro Glu Ala Gln Ala Ala Ala Ala Lys
            435                 440                 445

Ala Ala Lys Tyr Gly Val Gly Thr Pro Ala Ala Ala Ala Lys Ala
        450                 455                 460

Ala Ala Lys Ala Ala Gln Phe Gly Leu Val Pro Gly Val Gly Val Ala
465                 470                 475                 480

Pro Gly Val Gly Val Ala Pro Gly Val Gly Val Ala Pro Gly Val Gly
                485                 490                 495

Leu Ala Pro Gly Val Gly Val Ala Pro Gly Val Gly Val Ala Pro Gly
            500                 505                 510

Val Gly Val Ala Pro Gly Ile Gly Pro Gly Val Ala Ala Ala
            515                 520                 525

Lys Ser Ala Ala Lys Val Ala Ala Lys Ala Gln Leu Arg Ala Ala
530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
                565                 570                 575

Val Pro Gly Phe Gly Ala Val Pro Gly Ala Leu Ala Ala Ala Lys Ala
            580                 585                 590

Ala Lys Tyr Gly Ala Ala Val Pro Gly Val Leu Gly Gly Leu Gly Ala
        595                 600                 605

Leu Gly Gly Val Gly Ile Pro Gly Gly Val Val Gly Ala Gly Pro Ala
610                 615                 620

Ala Ala Ala Ala Ala Lys Ala Ala Ala Lys Ala Ala Gln Phe Gly
625                 630                 635                 640

Leu Val Gly Ala Ala Gly Leu Gly Gly Leu Gly Val Gly Gly Leu Gly
                645                 650                 655

Val Pro Gly Val Gly Gly Leu Gly Gly Ile Pro Pro Ala Ala Ala Ala
            660                 665                 670

Lys Ala Ala Lys Tyr Gly Ala Ala Gly Leu Gly Gly Val Leu Gly Gly
        675                 680                 685

Ala Gly Gln Phe Pro Leu Gly Gly Val Ala Ala Arg Pro Gly Phe Gly
690                 695                 700

Leu Ser Pro Ile Phe Pro Gly Gly Ala Cys Leu Gly Lys Ala Cys Gly
705                 710                 715                 720

Arg Lys Arg Lys

<210> SEQ ID NO 8
<211> LENGTH: 677
<212> TYPE: PRT
<213> ORGANISM: Homo sapiens
```

<220> FEATURE:
<221> NAME/KEY: MISC_FEATURE
<222> LOCATION: (1)..(677)
<223> OTHER INFORMATION: Elastin isoform b

<400> SEQUENCE: 8

```
Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Ala Leu Gly Pro
        35                  40                  45

Gly Gly Lys Pro Leu Lys Pro Val Pro Gly Gly Leu Ala Gly Ala Gly
    50                  55                  60

Leu Gly Ala Gly Leu Gly Ala Phe Pro Ala Val Thr Phe Pro Gly Ala
65                  70                  75                  80

Leu Val Pro Gly Gly Val Ala Asp Ala Ala Ala Ala Tyr Lys Ala Ala
                85                  90                  95

Lys Ala Gly Ala Gly Leu Gly Gly Val Pro Gly Val Gly Gly Leu Gly
                100                 105                 110

Val Ser Ala Gly Ala Val Val Pro Gln Pro Gly Ala Gly Val Lys Pro
            115                 120                 125

Gly Lys Val Pro Gly Val Gly Leu Pro Gly Val Tyr Pro Gly Gly Val
    130                 135                 140

Leu Pro Gly Ala Arg Phe Pro Gly Val Gly Val Leu Pro Gly Val Pro
145                 150                 155                 160

Thr Gly Ala Gly Val Lys Pro Lys Ala Pro Gly Val Gly Gly Ala Phe
                165                 170                 175

Ala Gly Ile Pro Gly Val Gly Pro Phe Gly Gly Pro Gln Pro Gly Val
            180                 185                 190

Pro Leu Gly Tyr Pro Ile Lys Ala Pro Lys Leu Pro Gly Gly Tyr Gly
        195                 200                 205

Leu Pro Tyr Thr Thr Gly Lys Leu Pro Tyr Gly Tyr Gly Pro Gly Gly
    210                 215                 220

Val Ala Gly Ala Ala Gly Lys Ala Gly Tyr Pro Thr Gly Thr Gly Val
225                 230                 235                 240

Gly Pro Gln Ala Ala Ala Ala Ala Ala Lys Ala Ala Ala Lys Phe
                245                 250                 255

Gly Ala Gly Ala Ala Gly Val Leu Pro Gly Val Gly Gly Ala Gly Val
            260                 265                 270

Pro Gly Val Pro Gly Ala Ile Pro Gly Ile Gly Gly Ile Ala Gly Val
        275                 280                 285

Gly Thr Pro Ala Ala Ala Ala Ala Ala Ala Ala Ala Lys Ala Ala
    290                 295                 300

Lys Tyr Gly Ala Ala Gly Leu Val Pro Gly Gly Pro Gly Phe Gly
305                 310                 315                 320

Pro Gly Val Val Gly Val Pro Gly Ala Gly Val Pro Gly Val Gly Val
                325                 330                 335

Pro Gly Ala Gly Ile Pro Val Val Pro Gly Ala Gly Ile Pro Gly Ala
            340                 345                 350

Ala Val Pro Gly Val Val Ser Pro Glu Ala Ala Lys Ala Ala Ala
        355                 360                 365

Lys Ala Ala Lys Tyr Gly Ala Arg Pro Gly Val Gly Val Gly Gly Ile
370                 375                 380
```

-continued

```
Pro Thr Tyr Gly Val Gly Ala Gly Gly Phe Pro Gly Phe Gly Val Gly
385                 390                 395                 400

Val Gly Gly Ile Pro Gly Val Ala Gly Val Pro Gly Val Gly Gly Val
            405                 410                 415

Pro Gly Val Gly Gly Val Pro Gly Val Gly Ile Ser Pro Glu Ala Gln
        420                 425                 430

Ala Ala Ala Ala Ala Lys Ala Ala Lys Tyr Gly Leu Val Pro Gly Val
            435                 440                 445

Gly Val Ala Pro Gly Val Gly Val Ala Pro Gly Val Gly Val Ala Pro
        450                 455                 460

Gly Val Gly Leu Ala Pro Gly Val Gly Val Ala Pro Gly Val Gly Val
465                 470                 475                 480

Ala Pro Gly Val Gly Val Ala Pro Gly Ile Gly Pro Gly Gly Val Ala
            485                 490                 495

Ala Ala Ala Lys Ser Ala Ala Lys Val Ala Ala Lys Ala Gln Leu Arg
        500                 505                 510

Ala Ala Ala Gly Leu Gly Ala Gly Ile Pro Gly Leu Gly Val Gly Val
            515                 520                 525

Gly Val Pro Gly Leu Gly Val Gly Ala Gly Val Pro Gly Leu Gly Val
        530                 535                 540

Gly Ala Gly Val Pro Gly Phe Gly Ala Val Pro Gly Ala Leu Ala Ala
545                 550                 555                 560

Ala Lys Ala Ala Lys Tyr Gly Ala Ala Val Pro Gly Val Leu Gly Gly
            565                 570                 575

Leu Gly Ala Leu Gly Gly Val Gly Ile Pro Gly Gly Val Val Gly Ala
        580                 585                 590

Gly Pro Ala Ala Ala Ala Ala Ala Lys Ala Ala Ala Lys Ala Ala
        595                 600                 605

Gln Phe Gly Leu Val Gly Ala Ala Gly Leu Gly Gly Leu Gly Val Gly
        610                 615                 620

Gly Leu Gly Val Pro Gly Val Gly Gly Leu Gly Gly Ile Pro Pro Ala
625                 630                 635                 640

Ala Ala Ala Lys Ala Ala Lys Tyr Gly Val Ala Ala Arg Pro Gly Phe
            645                 650                 655

Gly Leu Ser Pro Ile Phe Pro Gly Gly Ala Cys Leu Gly Lys Ala Cys
        660                 665                 670

Gly Arg Lys Arg Lys
        675

<210> SEQ ID NO 9
<211> LENGTH: 692
<212> TYPE: PRT
<213> ORGANISM: Homo sapiens
<220> FEATURE:
<221> NAME/KEY: MISC_FEATURE
<222> LOCATION: (1)..(692)
<223> OTHER INFORMATION: Elastin isoform c

<400> SEQUENCE: 9

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
```

```
                50                  55                  60
Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Ala Pro Ser
                115                 120                 125

Val Pro Gly Ala Val Val Pro Gln Pro Gly Ala Gly Val Lys Pro Gly
                130                 135                 140

Lys Val Pro Gly Val Gly Leu Pro Gly Val Tyr Pro Gly Gly Val Leu
145                 150                 155                 160

Pro Gly Ala Arg Phe Pro Gly Val Gly Val Leu Pro Gly Val Pro Thr
                165                 170                 175

Gly Ala Gly Val Lys Pro Lys Ala Pro Gly Val Gly Gly Ala Phe Ala
                180                 185                 190

Gly Ile Pro Gly Val Gly Pro Phe Gly Gly Pro Gln Pro Gly Val Pro
                195                 200                 205

Leu Gly Tyr Pro Ile Lys Ala Pro Lys Leu Pro Gly Gly Tyr Gly Leu
                210                 215                 220

Pro Tyr Thr Thr Gly Lys Leu Pro Tyr Gly Tyr Gly Pro Gly Gly Val
225                 230                 235                 240

Ala Gly Ala Ala Gly Lys Ala Gly Tyr Pro Thr Gly Thr Gly Val Gly
                245                 250                 255

Pro Gln Ala Ala Ala Ala Ala Ala Lys Ala Ala Ala Lys Phe Gly
                260                 265                 270

Ala Gly Ala Ala Gly Val Leu Pro Gly Val Gly Ala Gly Val Pro
                275                 280                 285

Gly Val Pro Gly Ala Ile Pro Gly Ile Gly Gly Ile Ala Gly Val Gly
                290                 295                 300

Thr Pro Ala Ala Ala Ala Ala Ala Ala Ala Lys Ala Ala Lys
305                 310                 315                 320

Tyr Gly Ala Ala Ala Gly Leu Val Pro Gly Gly Pro Gly Phe Gly Pro
                325                 330                 335

Gly Val Val Gly Val Pro Gly Ala Gly Val Pro Gly Val Gly Val Pro
                340                 345                 350

Gly Ala Gly Ile Pro Val Val Pro Gly Ala Gly Ile Pro Gly Ala Ala
                355                 360                 365

Val Pro Gly Val Val Ser Pro Glu Ala Ala Lys Ala Ala Ala Lys
370                 375                 380

Ala Ala Lys Tyr Gly Ala Arg Pro Gly Val Gly Val Gly Gly Ile Pro
385                 390                 395                 400

Thr Tyr Gly Val Gly Ala Gly Gly Phe Pro Gly Phe Gly Val Gly Val
                405                 410                 415

Gly Gly Ile Pro Gly Val Ala Gly Val Pro Gly Val Gly Gly Val Pro
                420                 425                 430

Gly Val Gly Gly Val Pro Gly Val Gly Ile Ser Pro Glu Ala Gln Ala
                435                 440                 445

Ala Ala Ala Ala Lys Ala Ala Lys Tyr Gly Leu Val Pro Gly Val Gly
                450                 455                 460

Val Ala Pro Gly Val Gly Val Ala Pro Gly Val Gly Val Ala Pro Gly
465                 470                 475                 480
```

-continued

```
Val Gly Leu Ala Pro Gly Val Gly Val Ala Pro Val Gly Val Ala
            485                 490                 495

Pro Gly Val Gly Val Ala Pro Gly Ile Gly Pro Gly Gly Val Ala Ala
        500                 505                 510

Ala Ala Lys Ser Ala Ala Lys Val Ala Ala Lys Ala Gln Leu Arg Ala
        515                 520                 525

Ala Ala Gly Leu Gly Ala Gly Ile Pro Gly Leu Gly Val Gly Val Gly
        530                 535                 540

Val Pro Gly Leu Gly Val Gly Ala Gly Val Pro Gly Leu Gly Val Gly
545                 550                 555                 560

Ala Gly Val Pro Gly Phe Gly Ala Val Pro Gly Ala Leu Ala Ala Ala
                565                 570                 575

Lys Ala Ala Lys Tyr Gly Ala Ala Val Pro Gly Val Leu Gly Gly Leu
                580                 585                 590

Gly Ala Leu Gly Gly Val Gly Ile Pro Gly Gly Val Val Gly Ala Gly
                595                 600                 605

Pro Ala Ala Ala Ala Ala Ala Lys Ala Ala Lys Ala Ala Gln
        610                 615                 620

Phe Gly Leu Val Gly Ala Ala Gly Leu Gly Gly Leu Gly Val Gly Gly
625                 630                 635                 640

Leu Gly Val Pro Gly Val Gly Gly Leu Gly Gly Ile Pro Pro Ala Ala
                645                 650                 655

Ala Ala Lys Ala Ala Lys Tyr Gly Val Ala Ala Arg Pro Gly Phe Gly
                660                 665                 670

Leu Ser Pro Ile Phe Pro Gly Gly Ala Cys Leu Gly Lys Ala Cys Gly
                675                 680                 685

Arg Lys Arg Lys
        690

<210> SEQ ID NO 10
<211> LENGTH: 711
<212> TYPE: PRT
<213> ORGANISM: Homo sapiens
<220> FEATURE:
<221> NAME/KEY: MISC_FEATURE
<222> LOCATION: (1)..(711)
<223> OTHER INFORMATION: Elastin isoform d

<400> SEQUENCE: 10

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Ala Pro Ser
            115                 120                 125
```

-continued

```
Val Pro Gly Ala Val Pro Gln Pro Gly Ala Gly Val Lys Pro Gly
    130                 135                 140
Lys Val Pro Gly Val Gly Leu Pro Gly Val Tyr Pro Gly Gly Val Leu
145                 150                 155                 160
Pro Gly Ala Arg Phe Pro Gly Val Gly Val Leu Pro Gly Val Pro Thr
                165                 170                 175
Gly Ala Gly Val Lys Pro Lys Ala Pro Gly Val Gly Ala Phe Ala
            180                 185                 190
Gly Ile Pro Gly Val Gly Pro Phe Gly Gly Pro Gln Pro Gly Val Pro
            195                 200                 205
Leu Gly Tyr Pro Ile Lys Ala Pro Lys Leu Pro Gly Gly Tyr Gly Leu
    210                 215                 220
Pro Tyr Thr Thr Gly Lys Leu Pro Tyr Gly Tyr Gly Pro Gly Gly Val
225                 230                 235                 240
Ala Gly Ala Ala Gly Lys Ala Gly Tyr Pro Thr Gly Thr Gly Val Gly
                245                 250                 255
Pro Gln Ala Ala Ala Ala Ala Lys Ala Ala Lys Phe Gly
            260                 265                 270
Ala Gly Ala Ala Gly Val Leu Pro Gly Val Gly Ala Gly Val Pro
    275                 280                 285
Gly Val Pro Gly Ala Ile Pro Gly Ile Gly Gly Ile Ala Gly Val Gly
    290                 295                 300
Thr Pro Ala Ala Ala Ala Ala Ala Ala Lys Ala Ala Lys
305                 310                 315                 320
Tyr Gly Ala Ala Ala Gly Leu Val Pro Gly Gly Pro Gly Phe Gly Pro
                325                 330                 335
Gly Val Val Gly Val Pro Gly Ala Gly Val Pro Gly Val Gly Val Pro
            340                 345                 350
Gly Ala Gly Ile Pro Val Val Pro Gly Ala Gly Ile Pro Gly Ala Ala
            355                 360                 365
Val Pro Gly Val Val Ser Pro Glu Ala Ala Ala Lys Ala Ala Ala Lys
    370                 375                 380
Ala Ala Lys Tyr Gly Ala Arg Pro Gly Val Gly Val Gly Gly Ile Pro
385                 390                 395                 400
Thr Tyr Gly Val Gly Ala Gly Gly Phe Pro Gly Phe Gly Val Gly Val
                405                 410                 415
Gly Gly Ile Pro Gly Val Ala Gly Val Pro Gly Val Gly Gly Val Pro
            420                 425                 430
Gly Val Gly Gly Val Pro Gly Val Gly Ile Ser Pro Glu Ala Gln Ala
            435                 440                 445
Ala Ala Ala Ala Lys Ala Lys Tyr Gly Val Gly Thr Pro Ala Ala
    450                 455                 460
Ala Ala Ala Lys Ala Ala Lys Ala Ala Gln Phe Gly Leu Val Pro
465                 470                 475                 480
Gly Val Gly Val Ala Pro Gly Val Gly Val Ala Pro Gly Val Gly Val
                485                 490                 495
Ala Pro Gly Val Gly Leu Ala Pro Gly Val Gly Val Ala Pro Gly Val
            500                 505                 510
Gly Val Ala Pro Gly Val Gly Val Ala Pro Gly Ile Gly Pro Gly Gly
            515                 520                 525
Val Ala Ala Ala Lys Ser Ala Ala Lys Val Ala Ala Lys Ala Gln
    530                 535                 540
Leu Arg Ala Ala Ala Gly Leu Gly Ala Gly Ile Pro Gly Leu Gly Val
```

```
                        545                 550                 555                 560

Gly Val Gly Val Pro Gly Leu Gly Val Gly Ala Gly Val Pro Gly Leu
                565                 570                 575

Gly Val Gly Ala Gly Val Pro Gly Phe Gly Ala Val Pro Gly Ala Leu
            580                 585                 590

Ala Ala Ala Lys Ala Ala Lys Tyr Gly Ala Ala Val Pro Gly Val Leu
        595                 600                 605

Gly Gly Leu Gly Ala Leu Gly Gly Val Gly Ile Pro Gly Gly Val Val
    610                 615                 620

Gly Ala Gly Pro Ala Ala Ala Ala Ala Ala Lys Ala Ala Ala Lys
625                 630                 635                 640

Ala Ala Gln Phe Gly Leu Val Gly Ala Ala Gly Leu Gly Gly Leu Gly
                645                 650                 655

Val Gly Gly Leu Gly Val Pro Gly Val Gly Gly Leu Gly Ile Pro
                660                 665                 670

Pro Ala Ala Ala Ala Lys Ala Ala Lys Tyr Gly Val Ala Ala Arg Pro
                675                 680                 685

Gly Phe Gly Leu Ser Pro Ile Phe Pro Gly Gly Ala Cys Leu Gly Lys
            690                 695                 700

Ala Cys Gly Arg Lys Arg Lys
705                 710

<210> SEQ ID NO 11
<211> LENGTH: 705
<212> TYPE: PRT
<213> ORGANISM: Homo sapiens
<220> FEATURE:
<221> NAME/KEY: MISC_FEATURE
<222> LOCATION: (1)..(705)
<223> OTHER INFORMATION: Elastin isoform e

<400> SEQUENCE: 11

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
        130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190
```

-continued

```
Gly Pro Phe Gly Gly Pro Gln Pro Gly Val Pro Leu Gly Tyr Pro Ile
            195                 200                 205
Lys Ala Pro Lys Leu Pro Gly Tyr Gly Leu Pro Tyr Thr Thr Gly
        210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
                245                 250                 255
Ala Ala Ala Ala Lys Ala Ala Ala Lys Phe Gly Ala Gly Ala Ala Gly
                260                 265                 270
Val Leu Pro Gly Val Gly Ala Gly Val Pro Gly Val Pro Gly Ala
        275                 280                 285
Ile Pro Gly Ile Gly Gly Ile Ala Gly Val Gly Thr Pro Ala Ala Ala
        290                 295                 300
Ala Ala Ala Ala Ala Ala Ala Lys Ala Ala Lys Tyr Gly Ala Ala Ala
305                 310                 315                 320
Gly Leu Val Pro Gly Gly Pro Gly Phe Gly Pro Gly Val Val Gly Val
                325                 330                 335
Pro Gly Ala Gly Val Pro Gly Val Gly Val Pro Gly Ala Gly Ile Pro
                340                 345                 350
Val Val Pro Gly Ala Gly Ile Pro Gly Ala Ala Val Pro Gly Val Val
        355                 360                 365
Ser Pro Glu Ala Ala Lys Ala Ala Ala Lys Ala Ala Lys Tyr Gly
        370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Gly Ile Pro Gly
                405                 410                 415
Val Ala Gly Val Pro Gly Val Gly Gly Val Pro Gly Val Gly Gly Val
                420                 425                 430
Pro Gly Val Gly Ile Ser Pro Glu Ala Gln Ala Ala Ala Ala Ala Lys
        435                 440                 445
Ala Ala Lys Tyr Gly Leu Val Pro Gly Val Gly Val Ala Pro Gly Val
        450                 455                 460
Gly Val Ala Pro Gly Val Gly Val Ala Pro Gly Val Gly Leu Ala Pro
465                 470                 475                 480
Gly Val Gly Val Ala Pro Gly Val Gly Val Ala Pro Gly Val Gly Val
                485                 490                 495
Ala Pro Gly Ile Gly Pro Gly Gly Val Ala Ala Ala Lys Ser Ala
                500                 505                 510
Ala Lys Val Ala Ala Lys Ala Gln Leu Arg Ala Ala Gly Leu Gly
        515                 520                 525
Ala Gly Ile Pro Gly Leu Gly Val Gly Val Pro Gly Leu Gly
        530                 535                 540
Val Gly Ala Gly Val Pro Gly Leu Gly Val Gly Ala Gly Val Pro Gly
545                 550                 555                 560
Phe Gly Ala Val Pro Gly Ala Leu Ala Ala Lys Ala Ala Lys Tyr
                565                 570                 575
Gly Ala Ala Val Pro Gly Val Leu Gly Gly Leu Gly Ala Leu Gly Gly
                580                 585                 590
Val Gly Ile Pro Gly Gly Val Val Gly Ala Gly Pro Ala Ala Ala Ala
        595                 600                 605
```

```
Ala Ala Ala Lys Ala Ala Ala Lys Ala Ala Gln Phe Gly Leu Val Gly
    610                 615                 620
Ala Ala Gly Leu Gly Gly Leu Gly Val Gly Gly Leu Gly Val Pro Gly
625                 630                 635                 640
Val Gly Gly Leu Gly Gly Ile Pro Pro Ala Ala Ala Lys Ala Ala
                645                 650                 655
Lys Tyr Gly Ala Ala Gly Leu Gly Gly Val Leu Gly Gly Ala Gly Gln
                660                 665                 670
Phe Pro Leu Gly Gly Val Ala Ala Arg Pro Gly Phe Gly Leu Ser Pro
            675                 680                 685
Ile Phe Pro Gly Gly Ala Cys Leu Gly Lys Ala Cys Gly Arg Lys Arg
    690                 695                 700
Lys
705
```